(12) United States Patent
Ferracane et al.

(10) Patent No.: US 11,965,071 B2
(45) Date of Patent: Apr. 23, 2024

(54) THERMOPLASTIC FILMS AND PRODUCTS WITH DIFFUSION-BASED COMPARTMENTALIZED ADDITIVE COMPONENTS

(71) Applicant: THE GLAD PRODUCTS COMPANY, Oakland, CA (US)

(72) Inventors: Dean A. Ferracane, Willowbrook, IL (US); Jeffrey S. Stiglic, Willowbrook, IL (US); Anthony A. Cisek, Willowbrook, IL (US); Jessica Greer, Willowbrook, IL (US); Jing Hong, San Jose, CA (US)

(73) Assignee: THE GLAD PRODUCTS COMPANY, Oakland, CA (US)

( * ) Notice: Subject to any disclaimer, the term of this patent is extended or adjusted under 35 U.S.C. 154(b) by 0 days.

(21) Appl. No.: 17/760,320

(22) PCT Filed: Feb. 17, 2021

(86) PCT No.: PCT/US2021/018305
§ 371 (c)(1),
(2) Date: Aug. 8, 2022

(87) PCT Pub. No.: WO2021/167936
PCT Pub. Date: Aug. 26, 2021

(65) Prior Publication Data
US 2023/0096385 A1    Mar. 30, 2023

Related U.S. Application Data

(60) Provisional application No. 62/978,897, filed on Feb. 20, 2020.

(51) Int. Cl.
| | | |
|---|---|---|
| *B65F 1/00* | (2006.01) | |
| *A61L 9/014* | (2006.01) | |
| *C08J 5/18* | (2006.01) | |

(52) U.S. Cl.
CPC .............. *C08J 5/18* (2013.01); *A61L 9/014* (2013.01); *B65F 1/0026* (2013.01); *C08J 2300/22* (2013.01)

(58) Field of Classification Search
CPC ....... B65F 1/0026; B65D 33/28; B65D 65/40; B65D 31/02; A61L 9/01; B31B 2170/20
See application file for complete search history.

(56) References Cited

U.S. PATENT DOCUMENTS

| | | |
|---|---|---|
| 9,745,126 B1 | 8/2017 | Cobler |
| 10,549,888 B2 | 2/2020 | Jean-Mary et al. |
| 2006/0110080 A1 | 5/2006 | Thomas et al. |
| 2015/0298862 A1* | 10/2015 | Borchardt ................. A61F 7/08 383/112 |
| 2017/0008261 A1 | 1/2017 | Jean-Mary et al. |
| 2017/0362023 A1* | 12/2017 | Cobler .................... B65F 1/002 |
| 2018/0118415 A1* | 5/2018 | Jean-Mary .......... B31B 70/8134 |

FOREIGN PATENT DOCUMENTS

| | | |
|---|---|---|
| CN | 101331072 A | 12/2008 |
| CN | 105307692 A | 2/2016 |
| CN | 107848191 A | 3/2018 |
| CN | 109982725 A | 7/2019 |

OTHER PUBLICATIONS

International Search Report and Written Opinion dated Apr. 22, 2021, in International Application No. PCT/US2021/018305, 8 pages.
Examination Report as received in Canadian application 3,168,596 dated Nov. 24, 2022.
Office Action as received in Chinese application 2021800147945 dated Dec. 6, 2022.
Examination Report as received in Canadian application 3,168,596 dated Apr. 11, 2023.
Notice of Allowance as received in Canadian application 3,168,596 dated Sep. 21, 2023.

* cited by examiner

*Primary Examiner* — Gregory Listvoyb
(74) *Attorney, Agent, or Firm* — Keller Preece PLLC

(57) ABSTRACT

The present disclosure relates to thermoplastic films and products formed therefrom that include additive components effectively compartmentalized based on diffusion characteristics of the additive components. For example, first and second additive components are localized on a thermoplastic film in a manner that as the additive components diffuse, they minimize or avoid interaction. Specifically, the thermoplastic film is folded over itself to create an air gap that causes the additive components to desorb, diffuse into the air gap, and then absorb into the film at a position across the air gap rather than diffusing substantially laterally across the thermoplastic film. By ensuring that the additive components diffuse up and down rather than laterally and by laterally offsetting the additive components, one or more implementations effectively compartmentalize the antagonistic components.

20 Claims, 15 Drawing Sheets

THERMOPLASTIC FILMS AND PRODUCTS WITH DIFFUSION-BASED COMPARTMENTALIZED ADDITIVE COMPONENTS

CROSS-REFERENCE

This application is a 371 National Stage filing of international application PCT/US2021/18305, filed on Feb. 17, 2021, which claims the benefit of and priority to U.S. Provisional Application 62/978,897, filed on Feb. 20, 2020. The disclosures are herein incorporated by reference in their entirety.

BACKGROUND

Many consumer products formed from thermoplastic films, such as trash bags, food bags, feminine hygiene products, baby diapers, and adult incontinence products, are improved with odor control. Controlling malodors in connection with these and other products is often a significant concern. As a result, products are often scented to help mask (e.g., hide) the malodors that escape therefrom. Alternatively, or additionally, manufactures may add an odor neutralizing component to the product to neutralize any malodors.

Unfortunately, conventional odor control technologies often result in products that either have high-quality masking abilities (e.g., efficient fragrances) or high-quality odor neutralizing or trapping abilities. For example, odor-trapping technologies (e.g., activated carbon) and oxidative technologies (e.g., hydrogen peroxide) are both effective at neutralizing odors but both technologies can also counteract fragrances. In particular, many odor-trapping technologies will absorb perfume raw materials, thereby reducing the capacity of the odor-trapping technologies to trap malodor particles, while also reducing the intensity and effectiveness of the fragrance.

To allow for combinations of antagonistic technologies, some products include encapsulates or other material barriers. While such techniques can be effective at separating the odor neutralizing and odor masking materials, these techniques typically require additional processing, product redesign, and increased raw material costs. Due to these and other drawbacks, it is often undesirable or unfeasible to use encapsulates or other material barriers in many products.

Accordingly, there are a number of considerations to be made in controlling odors in connection with thermoplastic film products.

SUMMARY

One or more implementations of the present invention provide benefits and/or solve one or more of the foregoing or other problems in the art with thermoplastic films and products formed therefrom that include antagonistic additive technologies effectively compartmentalized without the need for additional materials or product redesign by leveraging diffusion characteristics of the additive components. For example, one or more implementations include two or more antagonistic odor controlling components localized on a product so that the antagonistic odor controlling technologies avoid or reduce interacting. More particularly, a first odor controlling component is localized on a thermoplastic film and a second, antagonistic odor controlling component is localized on the thermoplastic film such that as the first and second odor controlling components diffuse they minimize or avoid interaction. Specifically, by separating plies of the thermoplastic film by a small air gap, the odor controlling components desorb, diffuse into the air gap, and then absorb into the film ply across from an initial position. By helping ensure that the odor controlling components diffuse up and down rather than outwards, antagonistic odor controlling components that are laterally offset in a film stack are effectively compartmentalized. In one or more implementations, the air gaps are created by folding a thermoplastic film forming a product.

One or more implementations include a thermoplastic film product comprising a thermoplastic film folded one or more times to form a film stack. The layers of the film stack are separated by air gaps. The thermoplastic film product further comprises a first additive component localized at a first position on the thermoplastic film. The thermoplastic film product further comprises a second additive component localized at a second position on the thermoplastic film. The second additive component is antagonistic to the first additive component. Additionally, the second position of the second additive component is laterally offset from the first position of the first additive component. Furthermore, the first additive component diffuses to positions directly above and below the first position in the film stack without substantially diffusing to the second position or positions directly above or below the second position. In one or more implementations, the first additive component is an odor masking component and the second additive component is an odor neutralizing component.

One or more further implementations include a thermoplastic bag comprising a first sidewall and a second sidewall opposite the first sidewall. The first and second sidewalls are joined along a first side edge, an opposite second side edge, and a bottom edge. The thermoplastic bag further includes a first additive component localized at a first position on the first and second sidewalls and a second additive component localized at a second position on the first and second sidewalls. The second position is laterally offset from the first position. The thermoplastic bag also includes a first fold proximate the first position and a second fold proximate the second position. The thermoplastic bag further includes one or more additional positions on the first and second sidewalls directly above or below the first position to which the first additive component has diffused. The thermoplastic bag also includes one or more further positions on the first and second sidewalls directly above or below the second position to which the second additive component has diffused.

Additionally, one or more implementations include a method of manufacturing a thermoplastic bag. The method involves providing a thermoplastic film. The method also involves applying a first additive component to the thermoplastic film at a first position and applying a second additive component to the thermoplastic film at a second position. The method further involves folding the thermoplastic film one or more times over itself in a manner that the first and second positions remain laterally offset from one another. Additionally, due to the configuration of the folded thermoplastic film, the first additive component diffuses to one or more additional positions directly above or below the first position without substantially diffusing to the second position. Similarly, the second additive component diffuses to one or more further positions directly above or below the second position without substantially diffusing to the first position. The method also involves forming the thermoplastic film into a bag.

Additional features and advantages of exemplary implementations of the present invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above recited and other advantages and features of the present disclosure can be obtained, a more particular description of the present disclosure briefly described above will be rendered by reference to specific implementations thereof which are illustrated in the appended drawings. It should be noted that the figures are not drawn to scale, and that elements of similar structure or function are generally represented by like reference numerals for illustrative purposes throughout the figures. Understanding that these drawings depict only typical implementations of the present disclosure and are not therefore to be considered to be limiting of its scope, the present disclosure will be described and explained with additional specificity and detail through the use of the accompanying drawings in which.

DETAILED DESCRIPTION

Figure 1:
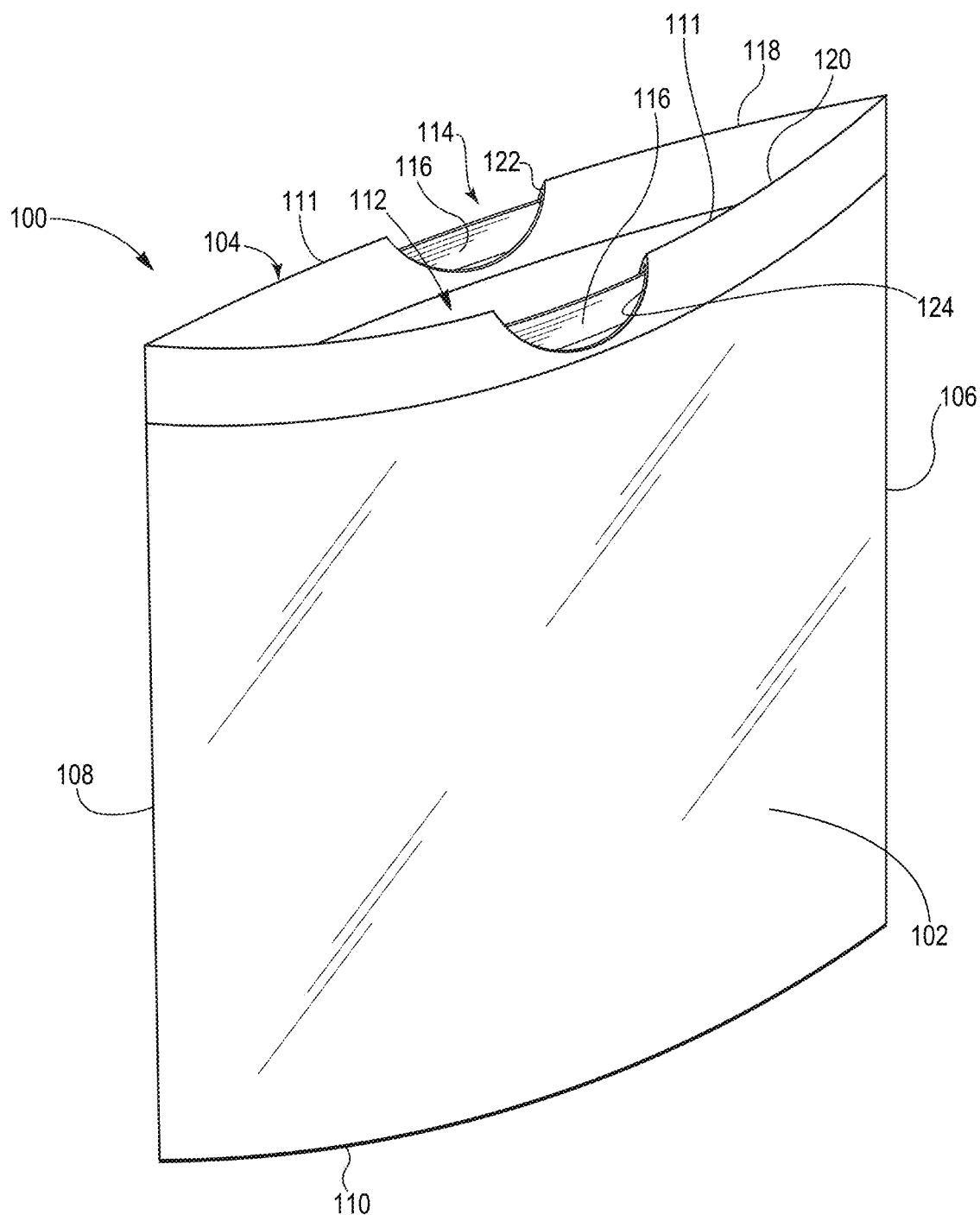
FIG. 1 shows a perspective view of a thermoplastic bag in accordance with one or more implementations.

One or more implementations of the present disclosure include thermoplastic films and products formed therefrom that include additive components effectively compartmentalized based on diffusion characteristics of the additive components. For example, antagonistic additive components are localized on a thermoplastic film in a manner that as the antagonistic additive components diffuse, they minimize or avoid interaction. Specifically, the thermoplastic film is folded over itself one or more times to create air gaps that cause the additive components to desorb, diffuse into an air gap, and then absorb into the film at a position across from the air gap rather than diffusing substantially laterally across the thermoplastic film. By ensuring that the additive components diffuse up and down rather than laterally, and by laterally offsetting the additive components, one or more implementations effectively compartmentalize the antagonistic additive components.

One or more implementations effectively compartmentalize antagonistic additive components. In other words, one or more implementations include a thermoplastic film with additive components localized or placed in positions relative to each other and folded portions of the thermoplastic film to help ensure that interaction between the additive components is limited or prevented. The additive components are effectively compartmentalized in that they do not substantially interact without encapsulation or other material barriers. Indeed, by leveraging diffusion characteristics, one or more implementations allow for effective compartmentalization of antagonistic additive components without having to revise the manufacture or design of a product.

As mentioned above, one or more implementations leverage diffusion characteristics of additive components to effectively compartmentalize the additive components. In particular, one or more implementations include placing volatile additive components on a thermoplastic film and then folding the thermoplastic film about itself so as to create air gaps between layers of the thermoplastic film. The volatility of the additive components and the small air gap between the layers can cause the additive components to desorb, diffuse into the air gaps, and then absorb into the thermoplastic film directly across from an initial position. Thus, the configuration of the additive components, folds of the thermoplastic film, and the air gaps can cause the additive components to diffuse up and down rather than laterally along the film. In view of this, one or more implementations can effectively compartmentalize by laterally offsetting the additive components.

One or more implementations include antagonistic additive components. In other words, one or more implementations include additive components that when exposed to each other cause a reduction in effectiveness of one or more of the additive components. For example, the additive components can comprise an odor-neutralizing additive component and an odor-masking additive component. One will appreciate that the additive components need not be odor-control components or even antagonistic. Indeed, in one or more implementations the additive components can provide for the creation or avoidance of color changes, enhanced product stability, antimicrobial performance etc. For example, in the case of additive components that when combined cause a color change, effectively compartmentalizing the additive components can delay a color change or avoid a color change. Furthermore, one or more implementations can involve one, two, three, four, or more additive components, some or all of which may be antagonistic.

As described above, the diffusion characteristics of volatile additive components can allow for effective compartmentalization of the additive components. As such, at least one of the additive components can comprise a volatile additive component. For example, one or more implementations can include a volatile additive component and a non-volatile additive component. The volatile additive component can be laterally offset from the non-volatile additive component to help ensure that the volatile additive component does not spread to the position of the non-volatile additive component. Sill further implementations can include two volatile additive components that are laterally offset to help ensure that the first volatile additive component does not spread to the position of the second volatile additive component, or vice-versa.

To help ensure that additive components diffuse up and down rather than laterally, one or more implementations involve creating small air gaps between layers. As discussed above, the air gaps can be created by folding a thermoplastic film about itself. Furthermore, the number, location, and configuration of the folds can all be used for the tailoring of products by controlling where additive components diffuse. In alternative implementations, the air gaps can be created by forming products with multiple layers that are separated, at least incrementally by air gaps.

In one or more implementations, the additive components is coextruded with the thermoplastic material so that the additive components is embedded into the material itself. In some implementations, the additive components is applied to the thermoplastic material after extrusion (e.g., using a liquid or a powder application). For example, the additive components can be applied to the thermoplastic material in solid form, liquid form, slurry form, as a solution, etc. Additionally, the additive components can be disposed onto a surface of the thermoplastic material (e.g., in a pattern—such as a strip, a spot, a series of dots, or other predetermined pattern—or as a complete layer covering the surface), within a hem of the thermoplastic material, or between a first layer and a second layer of the thermoplastic material.

As illustrated by the foregoing discussion, the present disclosure utilizes a variety of terms to describe features and benefits of one or more implementations. Additional detail is now provided regarding the meaning of these terms.

As used herein, the term "additive component" refers to component that can be optionally added to a thermoplastic film or product. An additive component can provide one or more benefits. For example, additive components can comprise odor control components (odor neutralizing or odor masking components), color changing components, antimicrobial components, liquid absorption components, cleaning components, etc. Additional additives that may be included in one or more implementations include slip agents, antiblock agents, voiding agents, or tackifiers. Further additives that may include in one or more implementations include natural oils. For example, the additives may include thyme oil, mint oil, lemon grass oil, tea tree oil, cinnamon bark oil, methyl jasmonate, etc. Yet further additives may include zinc pyrithione ("ZPT") and copper pyrithione ("CPT"), which inhibit microbial growth.

As mentioned above, an additive component can comprise an odor-control component. As used herein, the term "odor-control component" refers to a composition that affects (e.g., changes and/or masks) odors in at least one manner. For example, the odor-control component can absorb (e.g., foul smell odors) and/or may include fragrance materials. Furthermore, the odor-control component can mask (e.g., cover up) and/or neutralize malodors. As used herein the term "neutralize" or any of its derivative terms refers to an ability of a compound or product to reduce or eliminate malodorous compounds. Odor neutralization may be partial, affecting only some of the malodorous compounds in a given context, or affecting only a portion of a malodorous compound. A malodorous compound may be neutralized by chemical reaction resulting in a new chemical entity, by sequestration, by chelation, by association, or by any other interaction rendering the malodorous compound less malodourous or non-malodorous.

For example, the odor-control component can include one or more gaseous, liquid, colloidal suspension, and/or solid substances. In one or more implementations, the odor-control component includes a volatile fragrance material (i.e., a fragrance material capable of being transported to the olfactory system). For example, the odor-control component can include top, middle, and/or bottom notes of a fragrance composed of aromatic materials and other functional groups (e.g., ketones, aldehydes, alcohols, etc.). As used herein the term "fragrance" refers to any mixture or composition comprising one or more perfume raw materials with or without one or more carrier solvents configured to emit a pleasant odor.

In one or more implementations, the odor-control component comprises functional perfume raw materials (e.g., neutralizing chemistries—such as reactive aldehydes—or perceptual modifiers—such as receptor blockers). As used herein the term "perfume" refers to a compound utilized for its appealing odor. Compounds may have a pleasing odor without being used as a perfume in the context of this disclosure.

In further implementations, the odor-control component comprises one or more neutralizing agents. For example, in some implementations, the odor-control component includes oxidizing chemistries (e.g., peroxides, hypochlorous acid, chlorine, ozone, sodium perborate, etc.). As a further non-limiting example, the odor control component can comprise magnesium intercalated bleach (a.k.a. "MIB") as disclosed by U.S. Pat. No. 9,040,475, the contents of which are hereby incorporated herein by reference in their entirety.

In some implementations, the odor-control component comprises antimicrobial agents. For example, the odor-control component can include zinc pyrithione ("ZPT") and/or copper pyrithione ("CPT")). In some implementations, the odor-control component comprises vapor phase antimicrobials. For example, the odor-control component can comprise essential oils (e.g., thymol, lemongrass, tea tree, etc.), chlorine dioxide and/or ethylene oxide.

Moreover, the odor-control component can include one or more of desiccant materials (e.g., a hygroscopic substance, such as calcium oxide or silica gel, that has a high affinity for water and is used as a drying agent), deodorizing agents (i.e., deodorizing compositions with a deodorizing effect on offensive odors such as that associated with activated nitrogen compound, activated sulfur compounds, etc.), and functional nanoparticles. In yet further implementations, the odor-control component can include a trapping or an adsorbent/absorbent agent (e.g., zeolites, activated carbon, etc.).

As used herein, the term "odor" refers to any substance that can stimulate an olfactory response in a human; i.e., sense of smell. As used herein, the term "malodor" and any of its derivative terms refers to an odor that is generally considered unpleasant, obnoxious, or nauseating by the general population, such as the broad spectrum of odors associated with household trash, including odors related to stale urine, feces, vomitus, and putrefying organic materials, e.g., food waste, in common household trash. As used herein, the term "malodor particle" refers to a particle or molecule that elicits an unpleasant odor. Though it will be understood that a malodor particle includes any particle or molecule that elicits an unpleasant odor, examples of malodor particles include those derived from sulfide chemistries (e.g., dipropyl trisulfide, propyl mercaptan, dimethyl sulfide, dimethyl trisulfide, methal mercaptan, hydrogen sulfide, etc.), nitrogen chemistries (e.g., trimethylamine, trimethylamine, etc.), or aldehydes, keytones, and/or ester (e.g., demascenone, nonenal, pentanal, methinoal, pentyl acetate, etc.).

As used herein, the terms "lamination," "laminate," and "laminated film," refer to the process and resulting product made by bonding together two or more layers of film or other material. The term "bonding", when used in reference to bonding of multiple layers of a multi-layer film, may be used interchangeably with "lamination" of the layers. According to methods of the present disclosure, adjacent layers of a multi-layer film are laminated or bonded to one another. The bonding purposely results in a relatively weak bond between the layers that has a bond strength that is less than the strength of the weakest layer of the film. This allows the lamination bonds to fail before the film layer, and thus the bond, fails.

The term laminate is also inclusive of coextruded multi-layer films comprising one or more tie layers. As a verb, "laminate" means to affix or adhere (by means of, for example, adhesive bonding, pressure bonding, ultrasonic bonding, corona lamination, and the like) two or more separately made film articles to one another so as to form a multi-layer structure. As a noun, "laminate" means a product produced by the affixing or adhering just described.

As used herein the terms "partially discontinuous bonding" or "partially discontinuous lamination" refers to lamination of two or more layers where the lamination is substantially continuous in the machine direction or in the transverse direction, but not continuous in the other of the machine direction or the transverse direction. Alternately, partially discontinuous lamination refers to lamination of two or more layers where the lamination is substantially continuous in the width of the article but not continuous in the height of the article, or substantially continuous in the height of the article but not continuous in the width of the article. More particularly, partially discontinuous lamination refers to lamination of two or more layers with repeating bonded patterns broken up by repeating unbounded areas in either the machine direction or the transverse direction.

As used herein, the term "substantially," in reference to a given parameter, property, or condition, means to a degree that one of ordinary skill in the art would understand that the given parameter, property, or condition is met within a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "flexible" refers to materials that are capable of being flexed or bent, especially repeatedly, such that they are pliant and yieldable in response to externally applied forces. Accordingly, "flexible" is substantially opposite in meaning to the terms inflexible, rigid, or unyielding. Materials and structures that are flexible, therefore, may be altered in shape and structure to accommodate external forces and to conform to the shape of objects brought into contact with them without losing their integrity. In accordance with further prior art materials, web materials are provided which exhibit an "elastic-like" behavior in the direction of applied strain without the use of added traditional elastic. As used herein, the term "elastic-like" describes the behavior of web materials which when subjected to an applied strain, the web materials extend in the direction of applied strain, and when the applied strain is released the web materials return, to a degree, to their pre-strained condition.

As used herein, any relational terms such as "first," "second," and "third," "inner," "outer," "upper," "lower," "side," "top," "bottom," etc. are for clarity and convenience in understanding the present disclosure and accompanying drawings and does not connote or depend on any specific preference, orientation, or order, except where the context clearly indicates otherwise. For example, the relational terms may refer an orientation of a multi-layer bag while disposed within a receptacle (e.g., a trash can) for use.

As mentioned above, one or more implementations include thermoplastic films and products formed therefrom. Hereinafter is a description of exemplary thermoplastic materials and how to make such thermoplastic films. The thermoplastic material of the films of one or more implementations of the present disclosure may include thermoplastic polyolefins, including polyethylene and copolymers thereof and polypropylene and copolymers thereof. The olefin-based polymers may include ethylene or propylene based polymers such as polyethylene, polypropylene, and copolymers such as ethylene vinyl acetate (EVA), ethylene methyl acrylate (EMA) and ethylene acrylic acid (EAA), or blends of such polyolefins.

Other examples of polymers suitable for use as films in accordance with the present disclosure may include elastomeric polymers. Suitable elastomeric polymers may also be biodegradable or environmentally degradable. Suitable elastomeric polymers for the film include poly(ethylene-butene), poly(ethylene-hexene), poly(ethylene-octene), poly(ethylene-propylene), poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), oriented poly(ethylene-terephthalate), poly(ethylene-butylacrylate), polyurethane, poly(ethylene-propylene-diene), ethylene-propylene rubber, nylon, etc.

Some of the examples and description herein below refer to films formed from linear low-density polyethylene. The term "linear low density polyethylene" (LLDPE) as used herein is defined to mean a copolymer of ethylene and a minor amount of an olefin containing 4 to 10 carbon atoms, having a density of from about 0.910 to about 0.926, and a melt index (MI) of from about 0.5 to about 10. For example, some examples herein use an octene comonomer, solution phase LLDPE (MI=1.1; ρ=0.920). Additionally, other examples use a gas phase LLDPE, which is a hexene gas phase LLDPE formulated with slip/AB (MI=1.0; ρ=0.920). Still further examples use a gas phase LLDPE, which is a hexene gas phase LLDPE formulated with slip/AB (MI=1.0; ρ=0.926). One will appreciate that the present disclosure is not limited to LLDPE, and can include "high density polyethylene" (HDPE), "low density polyethylene" (LDPE), and "very low density polyethylene" (VLDPE). Indeed, films made from any of the previously mentioned thermoplastic materials or combinations thereof can be suitable for use with the present disclosure.

Some implementations of the present disclosure may include any flexible or pliable thermoplastic material that may be formed or drawn into a web or film. Furthermore, each thermoplastic film may include a single layer or multiple layers of thermoplastic materials. The thermoplastic material may be opaque, transparent, translucent, or tinted. Furthermore, the thermoplastic material may be gas permeable or impermeable.

An optional part of the film-making process is a procedure known as "orientation." The orientation of a polymer is a reference to its molecular organization, i.e., the orientation of molecules relative to each other. Similarly, the process of orientation is the process by which directionality (orientation) is imposed upon the polymeric arrangements in the film. The process of orientation is employed to impart desirable properties to films, including making cast films tougher (higher tensile properties). Depending on whether the film is made by casting as a flat film or by blowing as a tubular film, the orientation process can require different procedures. This is related to the different physical characteristics possessed by films made by the two conventional film-making processes; casting and blowing. Generally, blown films tend to have greater stiffness and toughness. By contrast, cast films usually have the advantages of greater film clarity and uniformity of thickness and flatness, generally permitting use of a wider range of polymers and producing a higher quality film.

When a film has been stretched in a single direction (monoaxial orientation), the resulting film can exhibit strength and stiffness along the direction of stretch, but can be weak in the other direction (i.e., across the stretch), often splitting when flexed or pulled. To overcome this limitation, two-way or biaxial orientation can be employed to more evenly distribute the strength qualities of the film in two directions. Most biaxial orientation processes use apparatus that stretches the film sequentially, first in one direction and then in the other.

In one or more implementations, the films of the present disclosure are blown film, or cast film. Blown film and cast film is formed by extrusion. The extruder used can be a conventional one using a die, which will provide the desired gauge. Some useful extruders are described in U.S. Pat. Nos. 4,814,135; 4,857,600; 5,076,988; 5,153,382; each of which are incorporated herein by reference in their entirety. Examples of various extruders, which can be used in producing the films to be used with the present disclosure, can be a single screw type modified with a blown film die, an air ring, and continuous take off equipment.

In one or more implementations, a manufacturer can use multiple extruders to supply different melt streams, which a feed block can order into different channels of a multi-channel die. The multiple extruders can allow a manufacturer to form a multi-layer film with layers having different compositions. Such multi-layer film may later be non-continuously laminated with another layer of film.

In a blown film process, the die can be an upright cylinder with a circular opening. Rollers can pull molten plastic upward away from the die. An air-ring can cool the film as the film travels upwards. An air outlet can force compressed air into the center of the extruded circular profile, creating a bubble. The air can expand the extruded circular cross section by a multiple of the die diameter. This ratio is called the "blow-up ratio." When using a blown film process, the manufacturer can collapse the film to double the plies of the film. Alternatively, the manufacturer can cut and fold the film, or cut and leave the film unfolded.

In any event, in one or more implementations, the extrusion process can orient the polymer chains of the blown film. In particular, the extrusion process can cause the polymer chains of the blown film to be predominantly oriented in the machine direction. The orientation of the polymer chains can result in an increased strength in the direction of the orientation. As used herein predominately oriented in a particular direction means that the polymer chains are more oriented in the particular direction than another direction. One will appreciate, however, that a film that is predominately oriented in a particular direction can still include polymer chains oriented in directions other than the particular direction. Thus, in one or more implementations the initial or starting films (films before being stretched or bonded or laminated in accordance with the principles described herein) can comprise a blown film that is predominately oriented in the machine direction.

The process of blowing up the tubular stock or bubble can further orient the polymer chains of the blown film. In particular, the blow-up process can cause the polymer chains of the blown film to be bi-axially oriented. Despite being bi-axially oriented, in one or more implementations the polymer chains of the blown film are predominantly oriented in the machine direction (i.e., oriented more in the machine direction than the transverse direction).

One of ordinary skill in the art will appreciate in view of the present disclosure that manufacturers may form the films or webs to be used with the present disclosure using a wide variety of techniques. For example, a manufacturer can form a precursor mix of the thermoplastic material and one or more additives. The manufacturer can then form the film(s) from the precursor mix using conventional flat or cast extrusion or coextrusion to produce monolayer, bilayer, or multilayer films. Alternatively, a manufacturer can form the films using suitable processes, such as, a blown film process to produce monolayer, bilayer, or multilayer films. If desired for a given end use, the manufacturer can orient the films by trapped bubble, tenterframe, or other suitable process. Additionally, the manufacturer can optionally anneal the films thereafter.

The films of one or more implementations of the present disclosure can have a starting gauge between about 0.1 mils to about 20 mils, suitably from about 0.2 mils to about 4 mils, suitably in the range of about 0.3 mils to about 2 mils, suitably from about 0.6 mils to about 1.25 mils, suitably from about 0.9 mils to about 1.1 mils, suitably from about 0.3 mils to about 0.7 mils, and suitably from about 0.4 mils and about 0.6 mils. Additionally, the starting gauge of films of one or more implementations of the present disclosure may not be uniform. Thus, the starting gauge of films of one or more implementations of the present disclosure may vary along the length and/or width of the film.

As an initial matter, one or more layers of the films described herein can comprise any flexible or pliable material comprising a thermoplastic material and that can be formed or drawn into a web or film. As described above, the film includes a plurality of layers of thermoplastic films. Each individual film layer may itself include a single layer or multiple layers. In other words, the individual layers of the multi-layer film may each themselves comprise a plurality of laminated layers. Such layers may be significantly more tightly bonded together than the bonding provided by the purposely weak discontinuous bonding in the finished multi-layer film. Both tight and relatively weak lamination can be accomplished by joining layers by mechanical pressure, joining layers with adhesives, joining with heat and pressure, spread coating, extrusion coating, and combinations thereof. Adjacent sub-layers of an individual layer may be coextruded. Coextrusion results in tight bonding so that the bond strength is greater than the tear resistance of the resulting laminate (i.e., rather than allowing adjacent layers to be peeled apart through breakage of the lamination bonds, the film will tear).

The following discussion provides more detail with regards to one or more implementations with reference to the figures. One or more implementations of the present disclosure include products made from or with thermoplastic films and that include additive components. For example, such products include, but are not limited to, grocery bags, trash bags, sacks, and packaging materials, feminine hygiene products, baby diapers, adult incontinence products, or other products. For ease in description, however, the figures and bulk of the following disclosure focuses on films and bags. One will further appreciate that the teachings and disclosure equally applies to other products as well. For example, some implementations of the present disclosure include nonwovens in place of the films described herein. Additional implementations of the present disclosure include other materials in place of the films described herein.

Referring now to the figures, FIG. 1 is a perspective view of a thermoplastic bag 100 according to an implementation of the present disclosure. The thermoplastic bag 100 includes a first sidewall 102 and a second sidewall 104. Each of the first and second sidewalls 102, 104 includes a first side edge 106, a second opposite side edge 108, a bottom edge 110 extending between the first and second side edges 106, 108, and top edge 111 extending between the first and second side edges 106, 108 opposite the bottom edge 110. In some implementations, the first sidewall 102 and the second sidewall 104 are joined together along the first side edges 106, the second opposite side edges 108, and the bottom edges 110. The first and second sidewalls 102, 104 may be joined along the first and second side edges 106, 108 and bottom edges 110 by any suitable process such as, for example, a heat seal.

In some implementations, the bottom edge 110 or one or more of the side edges 106, 108 can comprise a fold. In other words, the first and second sidewalls 102, 104 may comprise a single unitary piece of material. The top edges 111 of the first and second sidewalls 102, 104 may define an opening 112 to an interior of the thermoplastic bag 100. In other words, the opening 112 may be oriented opposite the bottom edge 110 of the thermoplastic bag 100. Furthermore, when placed in a trash receptacle, the top edges 111 of the first and second sidewalls 102, 104 may be folded over the rim of the receptacle.

In some implementations, the thermoplastic bag 100 may optionally include a closure mechanism 114 located adjacent to the top edges 111 for sealing the top of the thermoplastic bag 100 to form an at least substantially fully-enclosed container or vessel. As shown in FIG. 1, in some implementations, the closure mechanism 114 comprises a draw tape 116, a first hem 120, and a second hem 118. In particular, the first top edge 111 of the first sidewall 102 may be folded back into the interior volume and may be attached to an interior surface of the first sidewall 102 to form the first hem 120. Similarly, the second top edge 111 of the second sidewall 104 is folded back into the interior volume and may be attached to an interior surface of the second sidewall 104 to form a second hem 118. The draw tape 116 extends through the first and second hems 120, 118 along the first and second top edges 111. The first hem 120 includes a first aperture 124 (e.g., notch) extending through the first hem 120 and exposing a portion of the draw tape 116. Similarly, the second hem 118 includes a second aperture 122 extending through the second hem 118 and exposing another portion of the draw tape 116. During use, pulling the draw tape 116 through the first and second apertures 124, 122 will cause the first and second top edges 111 to constrict. As a result, pulling the draw tape 116 through the first and second apertures 124, 122 will cause the opening 112 of the multi-layer bag to at least partially close or reduce in size. The draw tape closure mechanism 114 may be used with any of the implementations of a reinforced thermoplastic bag described herein.

Although the thermoplastic bag 100 is described herein as including a draw tape closure mechanism 114, one of ordinary skill in the art will readily recognize that other closure mechanisms may be implemented into the thermoplastic bag 100. For example, in some implementations, the closure mechanism 114 may include one or more of flaps or handles, adhesive tapes, a tuck and fold closure, an interlocking closure, a slider closure, a zipper closure, or any other closure structures known to those skilled in the art for closing a bag.

Figure 2:
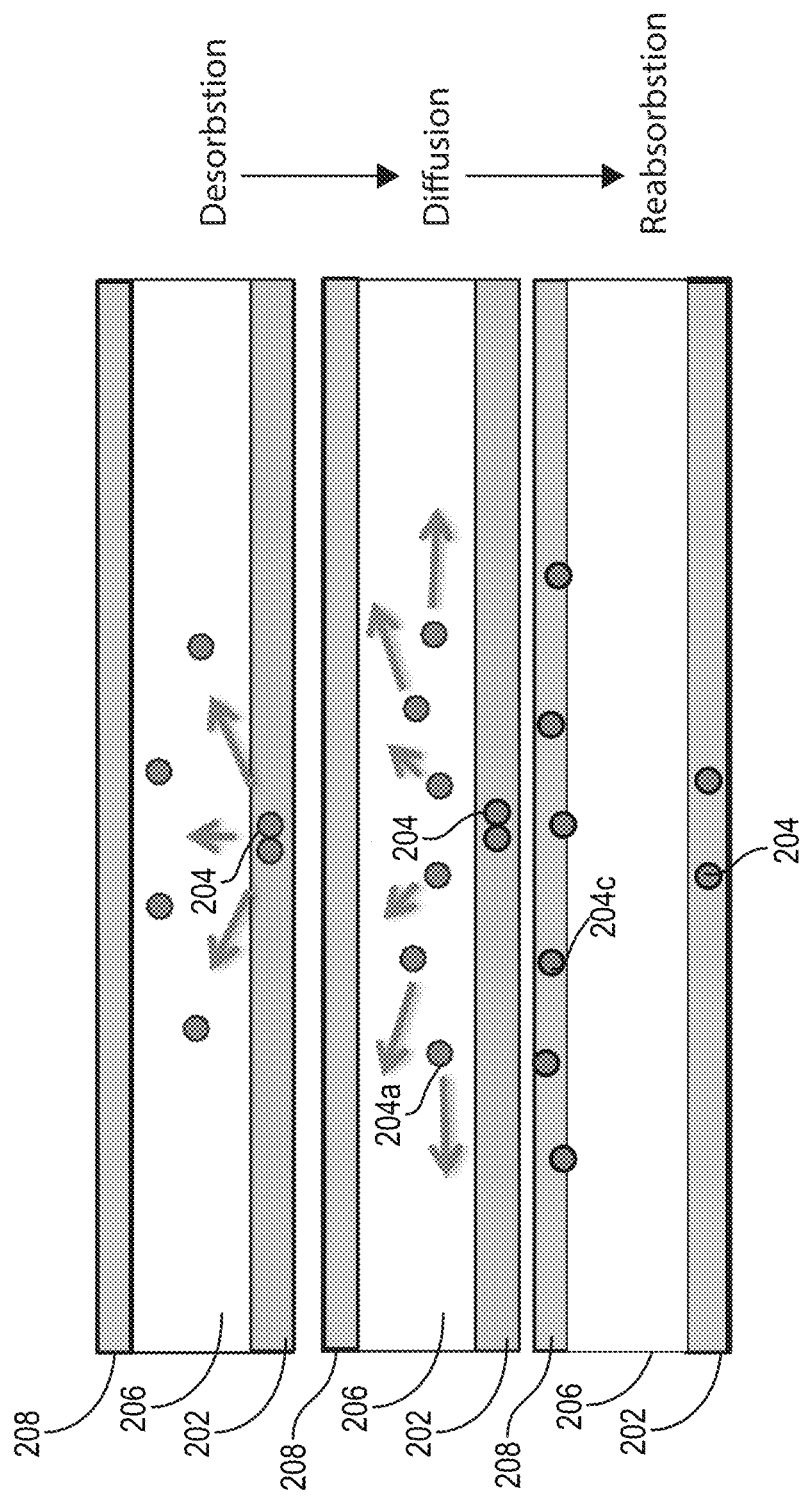
FIG. 2 illustrates a diffusion model of a volatile additive component in a film stack in accordance with one or more implementations.

In any event, one or more implementations involve applying additive components to a thermoplastic film (such as the sidewalls of the thermoplastic bag 100) and configuring the thermoplastic film to effectively compartmentalize the additive components based on diffusion characteristics of one or more of the additive components. In particular, FIG. 2 illustrates a first thermoplastic film layer 202 to which a volatile additive component 204 has been applied. The first thermoplastic film layer 202 is separated from a second thermoplastic film layer 208 by an air gap 206. The first and second thermoplastic film layers 202, 208 can be different portions of the same thermoplastic film positioned above each other by a fold or different thermoplastic films in a multi-film product.

As shown by FIG. 2, due to the volatile nature of the additive component 204 and the adjacent air gap 206, the additive component 204 can desorb from the first thermoplastic film layer 202. Then the desorbed additive component 204a can diffuse in the air gap 206. Finally, the additive component can reabsorb into the second thermoplastic film layer 208. As a result both the first and second thermoplastic film layers can include the additive component 204, 204c, respectively. Furthermore, the additive component 204c in the second thermoplastic film layer 208 can be directly across from the initial location of the additive component 204 in the first thermoplastic film layer 202.

Figure 3:
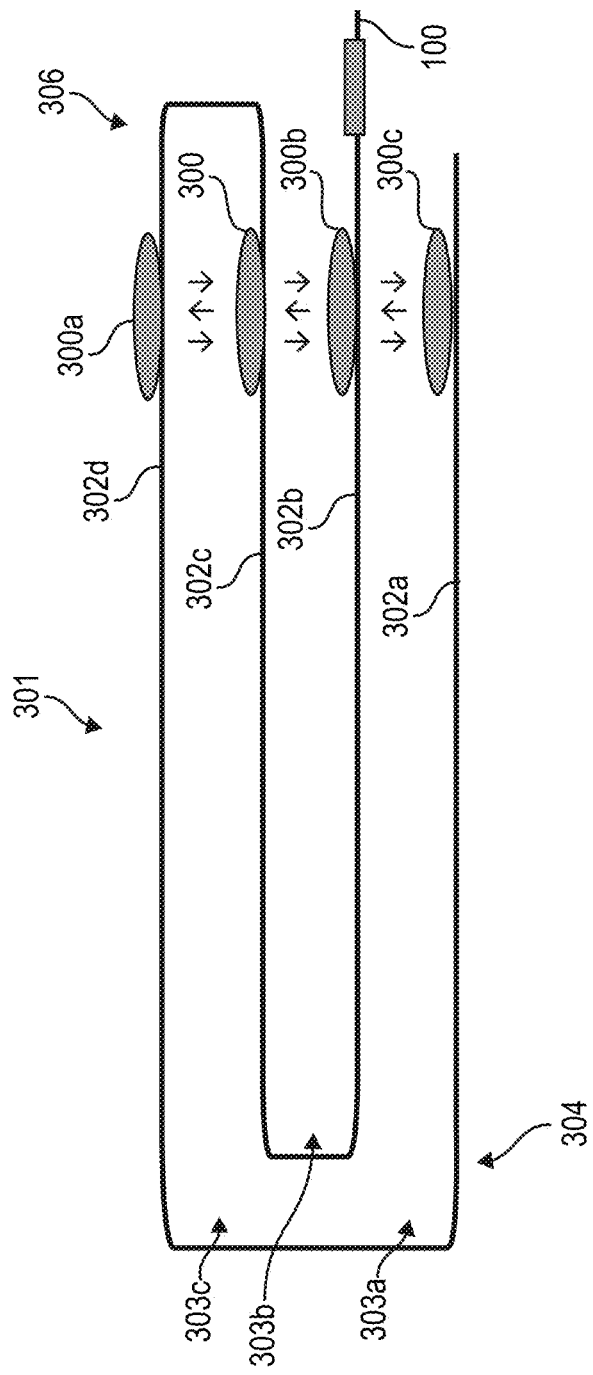
FIG. 3 illustrates a schematic diagram of a thermoplastic bag folded about itself and positions to which an additive component has diffused in accordance with one or more implementations.

Turning now to FIG. 3, a thermoplastic film (e.g., a thermoplastic bag 100) is folded one or more times about itself to form a film stack 301. As shown the layers 302a, 302b, 302c, 302d of the film stack 301 are separated by air gaps 303a, 303b, 303c. A first additive component is localized at a first position 300 on the thermoplastic film. As shown and as described in relation to FIG. 2, the first additive component has diffused from film layer 302*c* to additional positions 300*a*, 300*b*, 300*d* directly above or below the first position. As shown, the additional positions to which the first additive has diffused are separated from each other and the first position 300 by the air gaps 303*a*-303*c*. As shown the air gaps 303*a*-303*c* are created by a first fold 306 and a second fold 304.

As shown by FIG. 3, the first additive component has not diffused to the portions of the thermoplastic film proximate the second fold 304. As such, one or more implementations include a second additive component (e.g., an antagonistic additive component) proximate the second fold 304. Because the first additive component diffuses up and down and not substantially laterally, the first additive component is effectively compartmentalized to positions proximate the first fold 306 and away from the second additive component.

Figure 4:
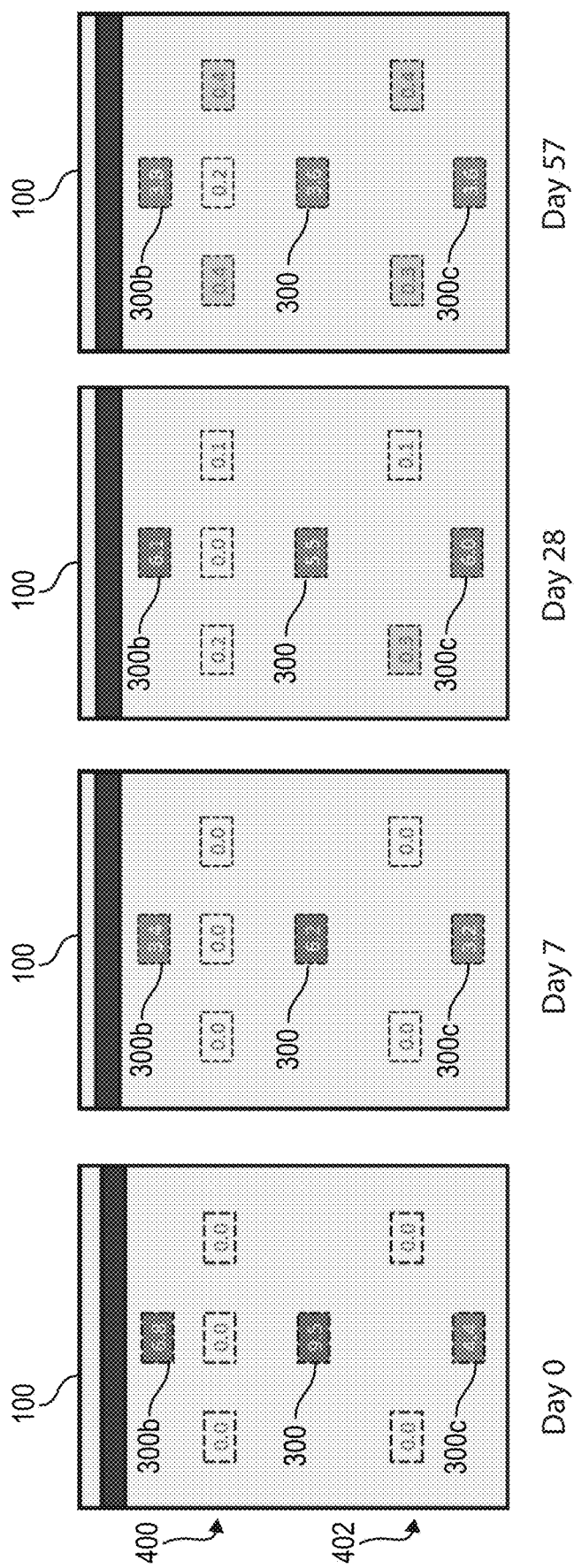
FIG. 4 illustrates how the additive component has diffused on the thermoplastic bag of FIG. 3 over time in accordance with one or more implementations.

FIG. 4 illustrates the results of a series of tests measuring how an additive component applied to a thermoplastic bag as shown in FIG. 3 diffused over time. In particular, FIG. 4 illustrates the results of applying a fragrance oil at position 300 and then measuring the fragrance intensity at several positions on the thermoplastic bag at 0 days, 7 days, 28 days, and 57 days respectively. As shown at day 0, the additive component applied at position 300 has a fragrance concentration of 9.5. Furthermore, the additive component has diffused to positions 300*b* and 300*c* where it has a fragrance concentration of 6.8 and 4.4 respectively. The first additive component did not diffuse to the top center 400 or the bottom center of the bag 402 (i.e., at positions laterally offset from the first position 300 when in a film stack) as the fragrance concentration measured at 0.0 at these locations. At seven days, the additive component was measured at positions 300, 300*b*, and 300*c*, but still not at positions 400 and 402. At day 28 and day 57, the additive component is still present at positions 300, 300*b*, and 300*c* and negligibly present at positions 400 and 402.

Figure 5:
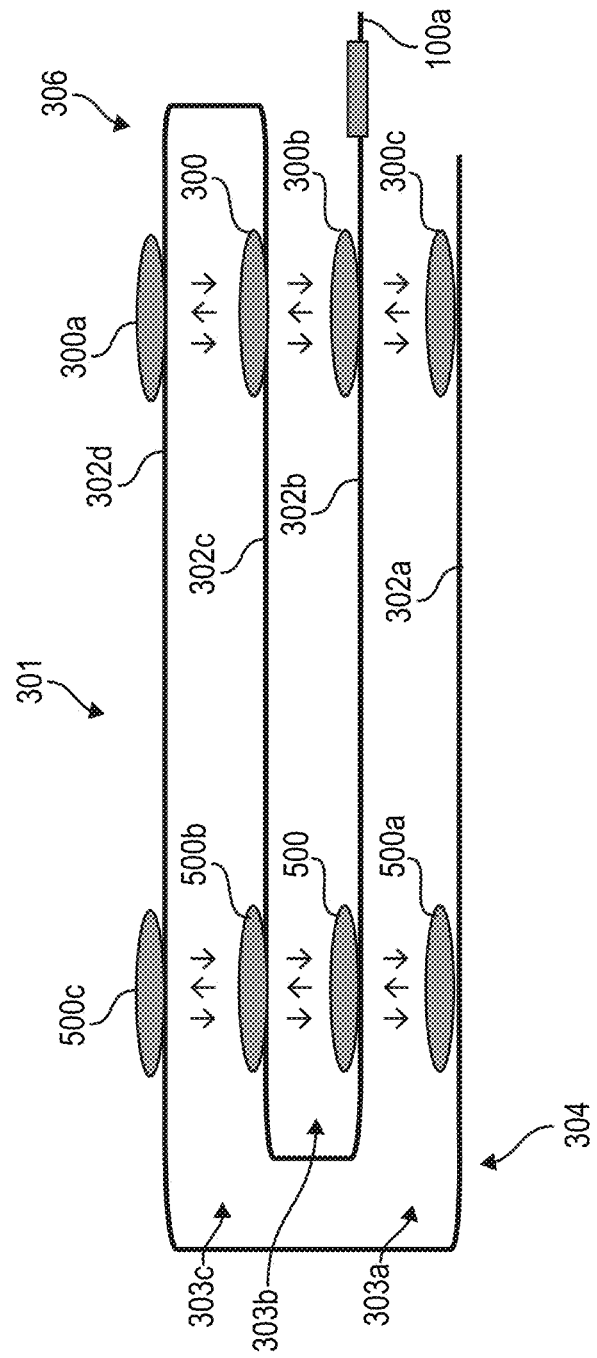
FIG. 5 illustrates a schematic diagram of a thermoplastic bag folded about itself and positions to which additive components have diffused in accordance with one or more implementations.

Turning now to FIG. 5, a thermoplastic film (e.g., a thermoplastic bag 100) is folded one or more times about itself to form a film stack 301 similar to that of FIG. 3. As shown the layers 302*a*, 302*b*, 302*c*, 302*d* of the film stack 301 are separated by air gaps 303*a*, 303*b*, 303*c*. A first additive component is localized at a first position 300 on the thermoplastic film. As shown and as described in relation to FIG. 2, the first additive component has diffused from film layer 302*c* to additional positions 300*a*, 300*b*, 300*d* directly above or below the first position. As shown, the additional positions to which the first additive has diffused are separated from each other and the first position 300 by the air gaps 303*a*-303*c*. As shown the air gaps 303*a*-303*c* are created by a first fold 306 and a second fold 304.

As shown by FIG. 5, a second additive component is localized at a second position 500 on the thermoplastic film. In one or more implementations, the second additive component is antagonistic to the first additive component. As shown, the second position 500 of the second additive component is laterally offset from the first position 300 of the first additive component and the additional positions 300*a*-300*c* to which the first additive component has diffused. The second additive component has diffused from film layer 302*b* to further positions 500*a*, 500*b*, 500*c* directly above or below the second position 500. As shown, the further positions to which the second additive component has diffused are separated from each other and the second position 500 by the air gaps 303*a*-303*c*. As shown the air gaps 303*a*-303*c* are created by a first fold 306 and a second fold 304. Furthermore, the second additive component has not substantially diffused to the first position 300 or the one or more additional positions 300*a*-300*c*.

As shown by FIG. 5, the first additive component has not diffused to the portions of the thermoplastic film wherein the second additive component has diffused due to the lateral offset of the first position 300 and the second position 500. Because the first additive component diffuses up and down and not substantially laterally, the first additive component is effectively compartmentalized to positions proximate the first fold 306 and away from the second additive component. Similarly, because the second additive component diffuses up and down and not substantially laterally, the second additive component is effectively compartmentalized to positions proximate the second fold 304 and away from the first additive component.

In one or more implementations, the first and second additive components are odor controlling components. For example, in one or more implementations, the first additive component is an odor masking component and the second additive component is an odor neutralizing component. Specifically, the first and second additive components can comprise, respectively, an oxidant and a fragrance, an absorbent and a fragrance, an acid and a base, a selectively activatable component and a trigger, or two or more different character fragrances.

Still further, the first odor-control component can include a deodorizing agent and the second odor-control component can include a volatile fragrance material. In another non-limiting example, the first odor-control component includes a deodorizing agent and the second odor-control component that includes an antimicrobial agent. Furthermore, in some implementations, an odor-control component includes a volatile fragrance material that can include a plurality of different components to render scents of different expressions (e.g., intensity and/character).

Figure 6:
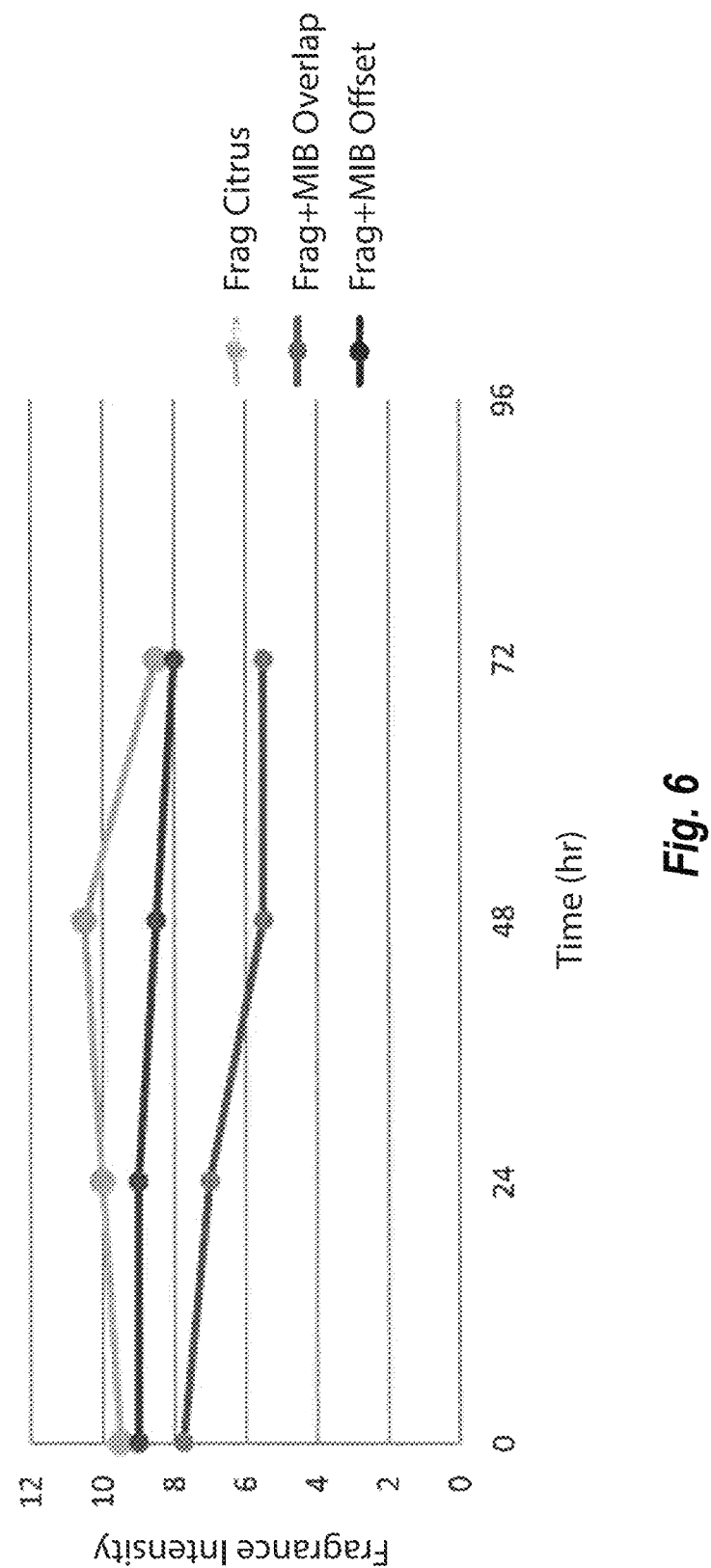
FIG. 6 illustrates a graph showing fragrance intensity over time on a thermoplastic film in the use cases of a fragrance additive only, a fragrance additive and an antagonistic oxidative additive overlapped, and a fragrance additive and an antagonistic oxidative additive offset in accordance with one or more implementations.

FIG. 6 illustrates the results of another test showing the effectiveness of one or more implementations. In particular, FIG. 6 illustrates a comparative study. In particular, in a first test, a fragrance was applied to a thermoplastic film and the fragrance intensity was measured at 0, 24, 48, and 72 hours.

In the second test, the same fragrance was applied along with MIB (an oxidative material that is known for its reactive odor control properties and that is antagonistic to fragrances). The MIB was positioned at an overlapping position relative to the position in which the fragrance was applied. In the third test, the same fragrance was applied along with MIB, however, the MIB was positioned at an offset position relative to the position in which the fragrance was applied.

As shown after 72 hours, the fragrance intensity was the strongest in test one, followed by test three with the offset MIB, followed by the second test with the overlapping MIB. More particularly, the fragrance intensity was 30% lower in test two with overlapping MIB versus test one at this time point, but less than 5% lower in test three with offset MIB versus test one. Even at the initial evaluation time point, the fragrance intensity was noticeably reduced in test two compared to test one and three. The results illustrated in FIG. 6 further establish how offsetting antagonistic additive components can effectively compartmentalize the additive components.

Figure 7:
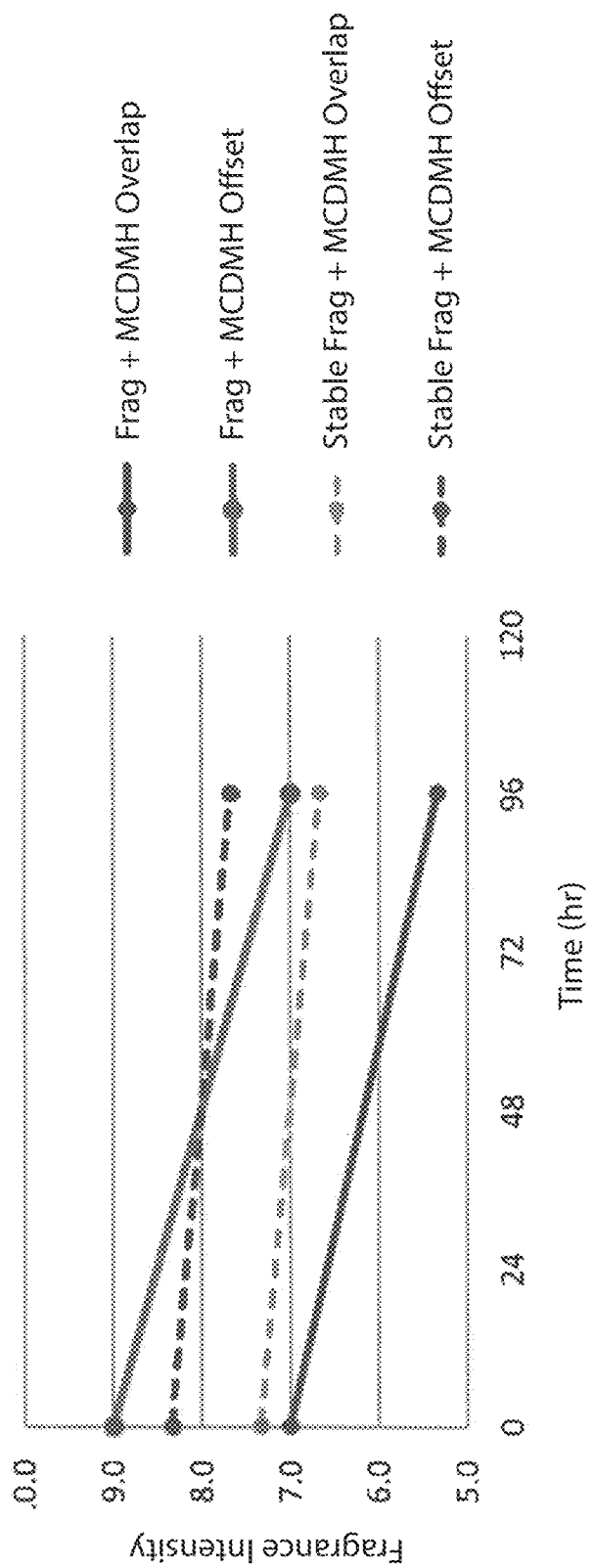
FIG. 7 illustrates a graph showing fragrance intensity over time on a thermoplastic film in the use cases of a fragrance additive and an antagonistic oxidative additive overlapped, a fragrance additive and an antagonistic oxidative additive offset, an oxidative-resistant fragrance and an oxidative additive overlapped, and an oxidative-resistant fragrance and an oxidative additive offset in accordance with one or more implementations.

FIG. 7 illustrates the results of another test showing the effectiveness of one or more implementations. In particular, FIG. 7 illustrates another comparative study. In particular, in a first test, a fragrance was applied to a thermoplastic film along with another stabilized oxidant, MCDMH (monochlorodimethylhydantoin). The MCDMH was positioned at an overlapping position relative to the position at which the fragrance was applied. In a second test comparative to the first test, the fragrance was applied to a thermoplastic film along with MCDMH. The MCDMH was positioned at an offset position relative to the position at which the fragrance was applied. In a third test, a stable fragrance was applied in an overlapping position relative to MCDMH. The stable fragrance comprises an oxidation-resistant fragrance. In a forth test, the stable fragrance was applied in an offset position relative to MCDMH.

As shown after 96 hours, the fragrance intensity was the strongest in both cases in the offset condition compared to the overlapping condition. Thus, the results illustrated in FIG. 7 further establish how offsetting antagonistic additive components can effectively compartmentalize the additive components. FIG. 7 further illustrates that the fragrance and offset MCDMH resulted in a higher fragrance intensity than the stable fragrance and MCDMH overlap case. As such, offsetting the fragrance and oxidant technology produces a better result than the use of an oxidation-resistant fragrance. The oxidation-resistant fragrances can leverage a less extensive palette of components, often resulting in higher formulation costs or fragrance character restrictions.

As noted above, the creation of small air gaps between layers of thermoplastic film helps ensure that additive components diffuse up and down rather than laterally. Furthermore, one or more implementations involve creating the air gaps by folding a thermoplastic film (e.g., a thermoplastic bag) on itself. The combination of localizing the additive components and configuring the folds can allow for the tailored effects. In particular, by configuring the number of folds and placement of the additive components, the total number of locations to which the additive components diffuse can be controlled.

Figure 8A:
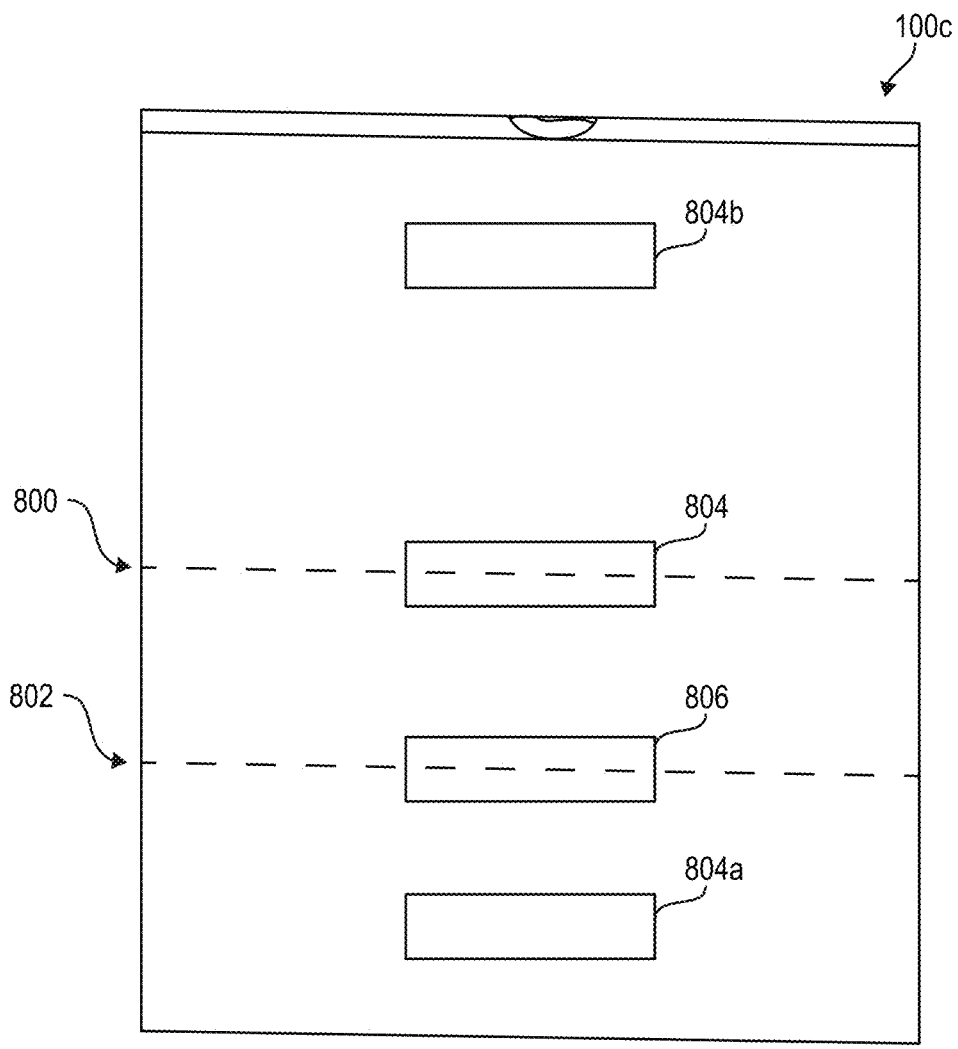
FIG. 8A illustrates a front view of a thermoplastic bag with folds and positions to which additive components have diffused in accordance with one or more implementations.

For example, FIG. 8A illustrates a view of a thermoplastic bag 100c with two folds. In particular, the thermoplastic bag 100c includes a first fold 800 and a second fold 802. Furthermore, FIG. 8A illustrates that when a first volatile additive component is localized at a first position 804 about the first fold 800, it will eventually diffuse to second and third positions 804a, 804b while substantially not diffusing to a fourth position 806 about the second fold 802 at which a second, antagonistic additive component may be localized. In the implementation shown in FIG. 8A, the second additive component may not be volatile, and thus, may not diffuse to other positions.

Figure 8B:
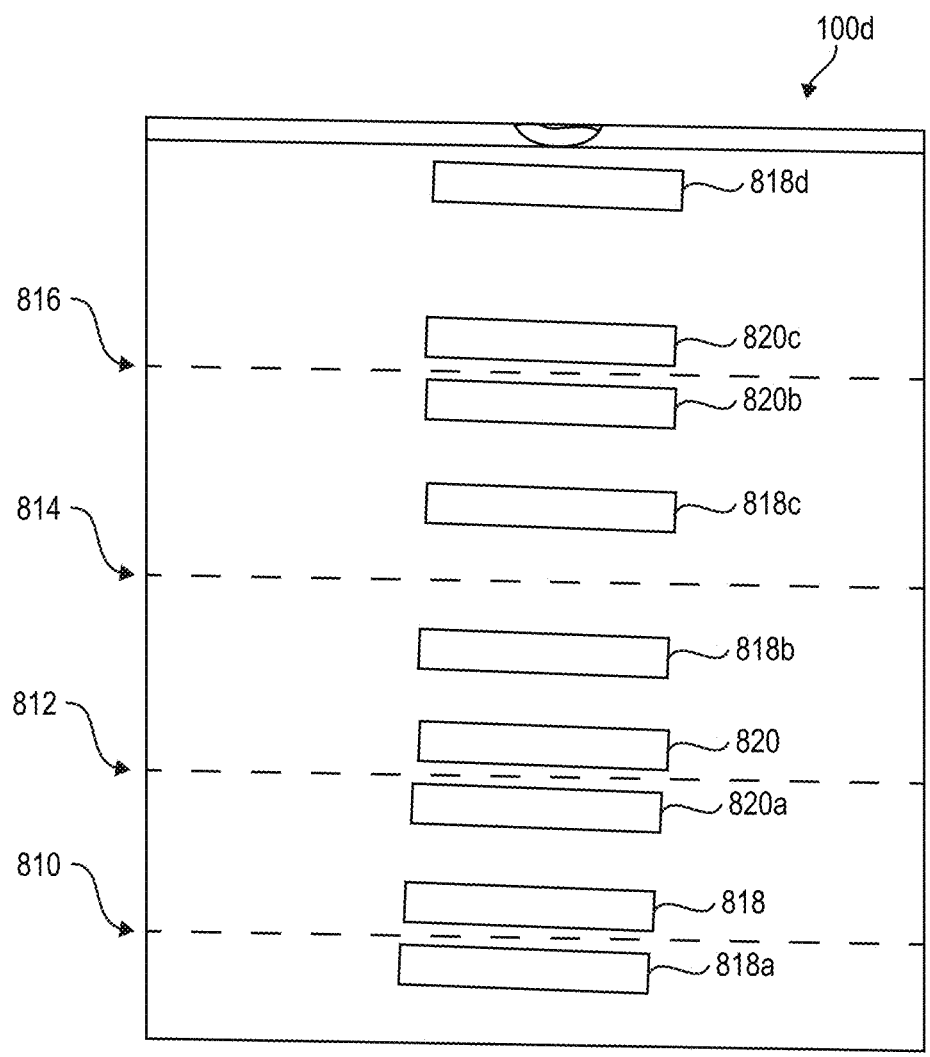
FIG. 8B illustrates a front view of another thermoplastic bag with folds and positions to which additive components have diffused in accordance with one or more implementations.

FIG. 8B illustrates another implementation of a thermoplastic bag 100d to which additive components can be applied. More particularly, the thermoplastic bag 100d includes four folds 810, 812, 814, and 816. The first two folds are in a first direction, while the second two folds are in an opposite direction. As shown, by placing a first volatile additive component at position 818 proximate the first fold, the first volatile additive component diffuses up or down to positions 818a, 818b, 818c, and 818d. Similarly, by placing a second volatile additive component at position 820 proximate the second fold, the second volatile additive component diffuses up or down to positions 820a, 820b, and 820c.

FIG. 8B further illustrates that by offsetting the first volatile additive component from the second volatile additive component, the first volatile additive component does not substantially diffuse to the offset position 820 at which the second volatile additive component is localized or the further locations 820a-820c to which the second volatile additive component diffuses. Similarly, the second volatile additive component does not substantially diffuse to the position 818 at which the first volatile additive component is localized or the additional locations 818a-818d to which the first volatile additive component diffuses.

As mentioned above, in addition to odor control components, one or more implementations includes color changing additive components. For example, in one or more implementations, a first additive component changes color as a result of oxidation. As an example, magnesium dioxide (a yellow/brown color) can produce a manganite ion (a green color) through oxidation, which can produce a permanganate ion (a purple color) through further oxidation. As another example, methylene blue turns a blue color when oxidized but becomes clear when reduced. In such implementations, the second additive component can comprise an oxidizer (e.g., MIB). The oxidizer can both activate the color changing component and neutralize odors. By offsetting the color changing additive and the oxidizer to effectively compartmentalize the additive components, the color changing can be delayed until the bag is in use.

Figure 9:
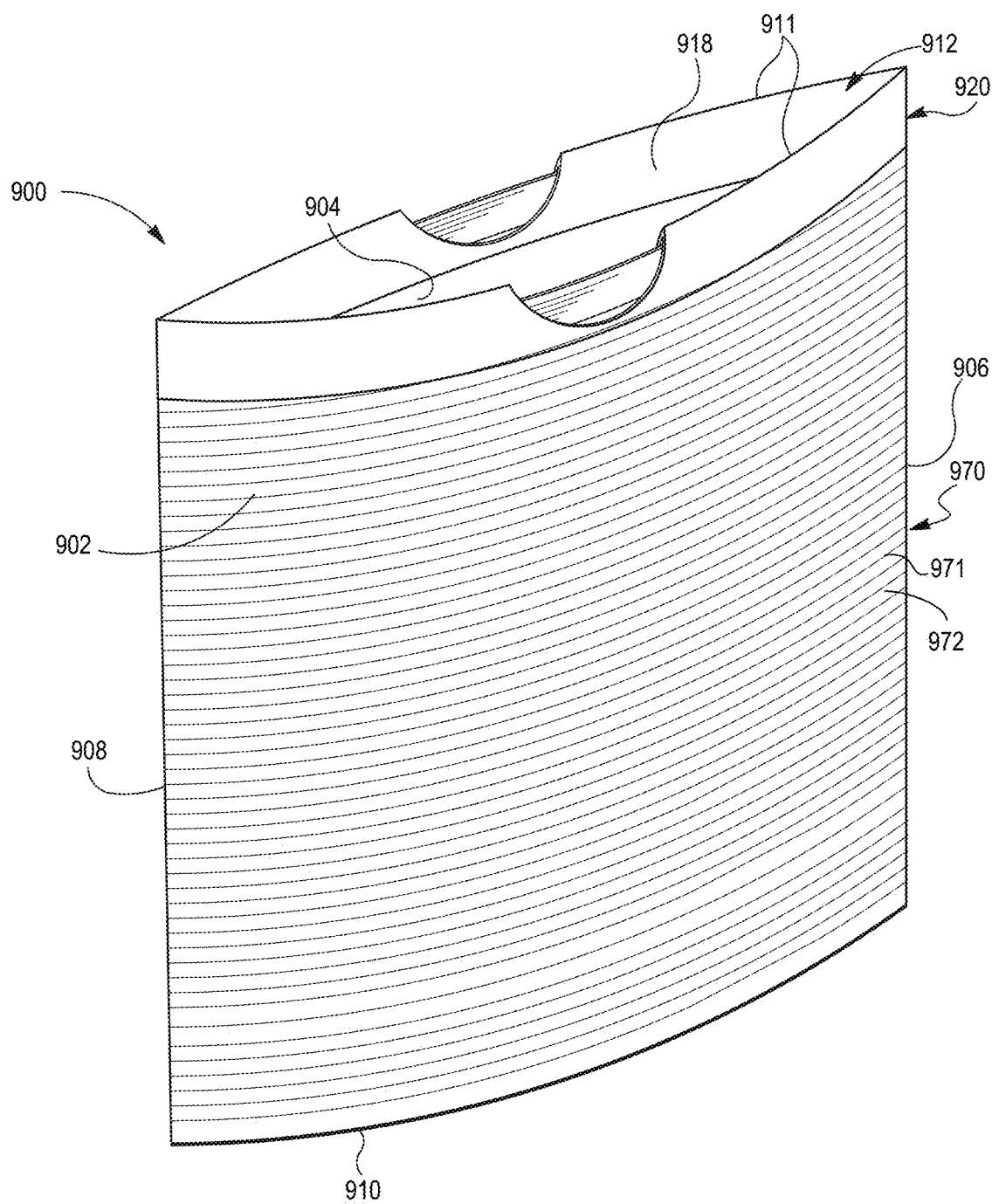
FIG. 9 illustrates a perspective view of a multi-layered thermoplastic bag having a pattern in accordance with one or more implementations.

The implementations described above involve the use of folds to create air gaps between layers of thermoplastic film to help ensure a desired diffusion pattern. Alternative implementations can involve multi-layered thermoplastic products where the layers have an air gap between them in addition or as an alternative to folds. For example, FIG. 9 illustrates a multi-layered thermoplastic bag 900. The multi-layered bag 900 is similar to the thermoplastic bag 100, albeit that the sidewalls 902, 904 are incrementally stretched and include multiple layers. In particular, the sidewalls 902, 904 include a ribbed pattern 970 of a plurality of alternating thinner (e.g., stretched) linear webs 971 and thicker linear ribs 972 that may extend across the sidewalls 902, 904 between the first side edge 906 and second side edge 908. As illustrated in FIG. 9, the webs 971 and ribs 972 may be parallel and adjacent to one another. Additionally, as illustrated in FIG. 9, the ribbed pattern 970 may extend from the bottom edge 910 toward the opening 912. To avoid interfering with the operation of the draw tape, the extension of the ribbed pattern 970 may terminate below the hems 918, 920. In alternative implementations, the ribbed pattern 970 can extend from the bottom edge 910 to the top edge 911 of each sidewall. The ribbed pattern 970 can be formed by passing the films of the sidewalls 902, 904 through a pair of transverse direction intermeshing ring rollers, such as those described in U.S. Pat. No. 9,669,595, the contents of which are hereby incorporated herein by reference in their entirety.

Figure 10:
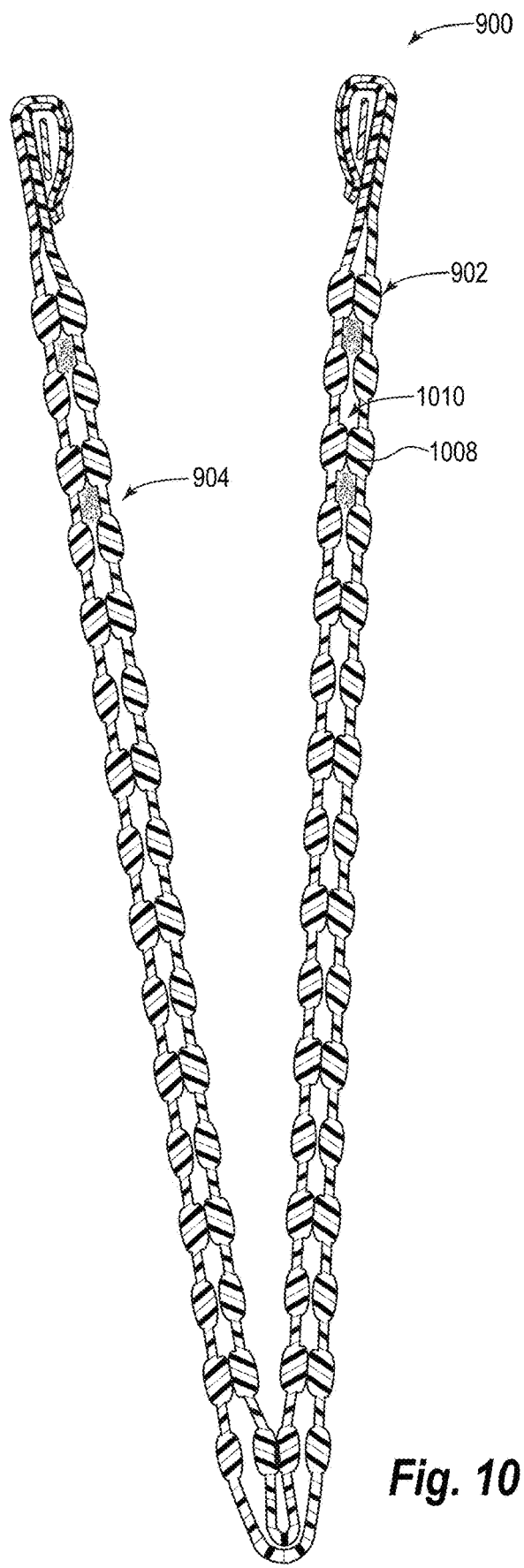
FIG. 10 illustrates a side cross-sectional view of the thermoplastic bag of FIG. 9 in accordance with one or more implementations.

FIG. 10 illustrates a side cross-sectional view of the thermoplastic bag 900 of FIG. 9. In particular, FIG. 10 shows the thermoplastic bag 900 wherein each of the sidewalls include multiple layers. As shown in FIG. 10, the multi-layer sidewalls of the thermoplastic bag 900 include bonded regions 1008 and un-bonded regions or air gaps 1010. In one or more implementations, the un-bonded regions or air gaps 1010 are located at each sidewall where the sidewall has been stretched or cold-formed (i.e., at the location of the stretched linear webs 971 discussed with reference to FIG. 9). In some implementations, the un-bonded regions or air gaps 1010 are located at each sidewall where the sidewall has not been stretched or cold-formed (i.e., at the location of the linear ribs 972 of FIG. 9). In some implementations, the bonded regions 1008 may comprise less than about 30 percent of a total area of the multi-layer sidewall. Furthermore, an additive component may be disposed within the un-bonded regions or air gaps 1010. Disposing the additive component within the un-bonded regions or air gaps 1010 allows the additive component to diffuse across the air gaps as described above.

In still further implementations, the one or more of the layers of the thermoplastic bag can be subjected to SELFing as described in U.S. Pat. Nos. 9,669,595; 5,518,801; 6,139,185; 6,150,647; 6,394,651; 6,394,652; 6,513,975; 6,695,476; U.S. Patent Application Publication No. 2004/0134923; and U.S. Patent Application Publication No. 2006/0093766, the entire contents of each of the foregoing patents and patent applications are hereby incorporated by reference.

Figure 11:
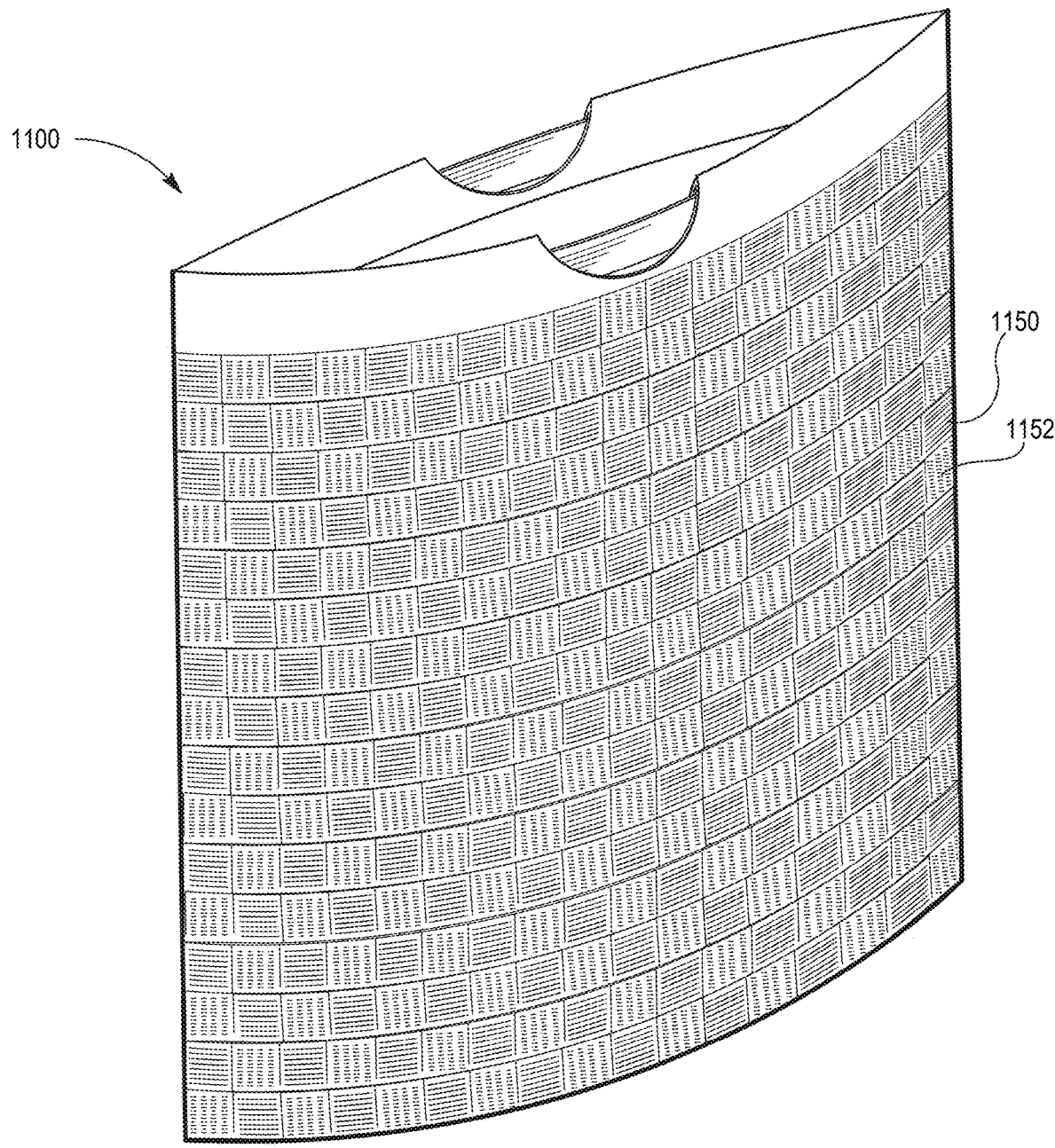
FIG. 11 illustrates a perspective view of thermoplastic bag having another pattern in accordance with one or more implementations.

FIG. 11 illustrates another thermoplastic bag 1100 similar to the thermoplastic bag 100 albeit with sidewalls that are SELF'ed. The thermoplastic bag 1100 can include the same structure as the thermoplastic bag 900 (e.g., one or more additive components offset from each other) albeit with a different pattern of intermittent bonds and thinner webs and thicker ribs. In particular, the thermoplastic bag 1100 may include a single pattern of raised like elements arranged in a checkerboard pattern. The pattern can comprise a micro pattern of raised rib-like elements 1152 and a macro pattern of raised rib-like elements 1150.

Figure 12A:
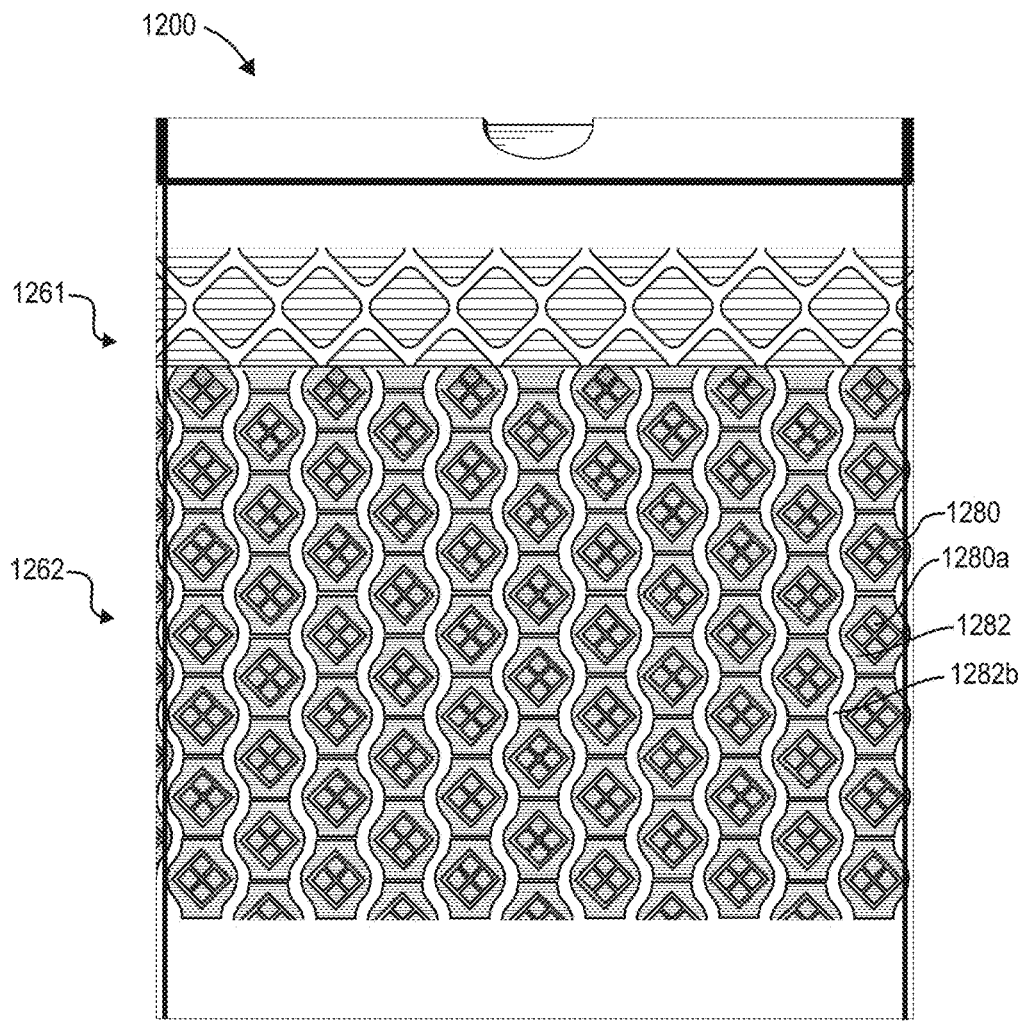
FIGS. 12A-12B illustrate a front view of a thermoplastic bag having yet another pattern in accordance with one or more implementations.
Figure 12B:
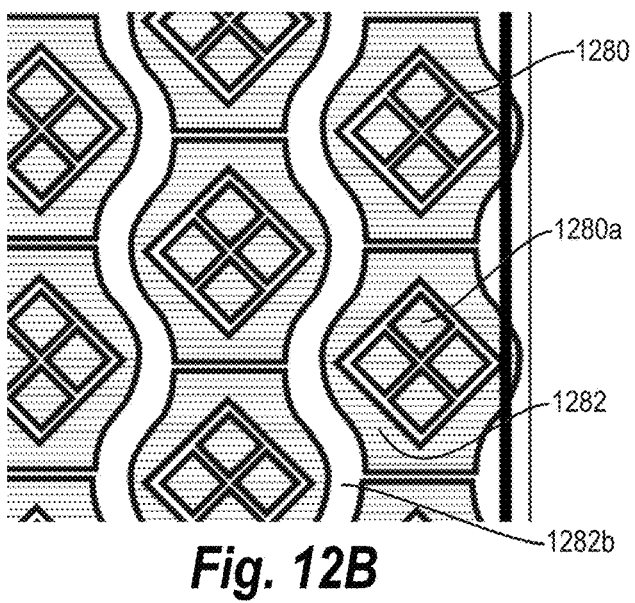

FIG. 12A shows another thermoplastic bag 1200 similar to the thermoplastic bag 100. FIG. 12B is an enlarged view of a portion of the thermoplastic bag 1200. Referring to FIGS. 12A and 12B together, one or more of the sidewalls of the thermoplastic bag 1200 have a first plurality of raised rib-like elements 1282 in a macro pattern (e.g., a bulbous pattern) and a second plurality of raised rib-like elements 1280a in a micro pattern (e.g., four diamonds) in a first middle portion 1262. As shown, the second plurality of raised rib-like elements 1280a in the micro pattern are nested within the macro patterns. Furthermore, the thermoplastic bag 1200 includes web areas 1280, 1282b. The web areas 1280, 1282b can surround the micro and the macro patterns of raised rib-like elements. The plurality of web areas 1280, 1282b comprise areas in which the first layer and the second layer are separated to form intermittent bonding between the layers (i.e., the inner bag and the outer bag). Furthermore, as shown by FIG. 12, the web areas 1282b are arranged in a sinusoidal pattern.

Additionally, FIG. 12 illustrates that the thermoplastic bags described herein can include areas with different patterns. In particular, FIG. 12 illustrates an upper potion 1261 of the thermoplastic bag 1200 including a fenced diamond pattern. The fenced diamond pattern can comprise raised-rib-like elements arranged in diamond patterns where the intersections of the sides of the diamond are rounded rather than ending in corners. The fenced diamond pattern can also comprise areas in which the first layer and the second layer are separated to form intermittent bonding between the layers (i.e., the inner bag and the outer bag).

Figure 13:
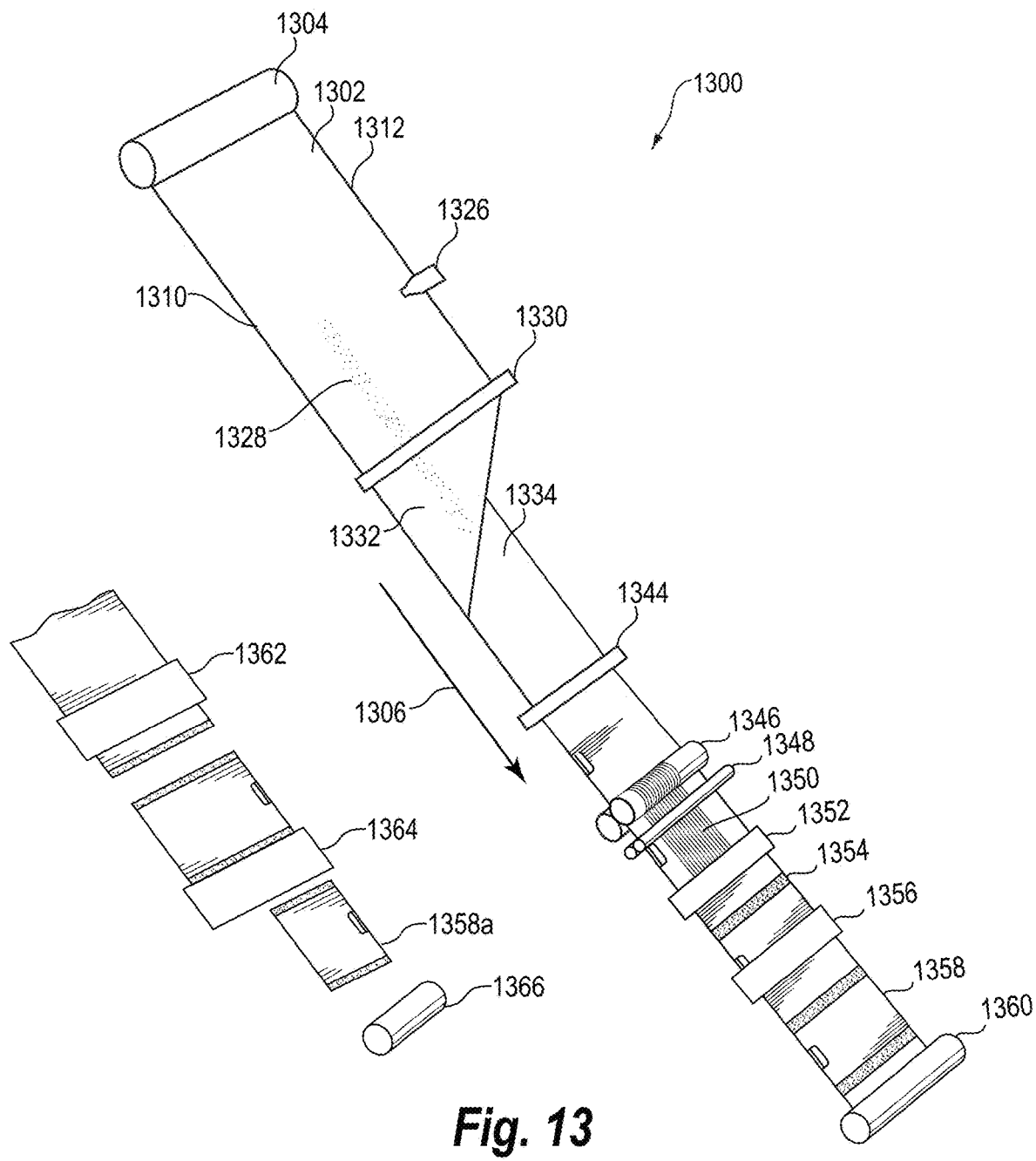
FIG. 13 illustrates a schematic diagram of a manufacturing process for producing thermoplastic bags having offset antagonistic additive components in accordance with one or more implementations.
Figure 14:
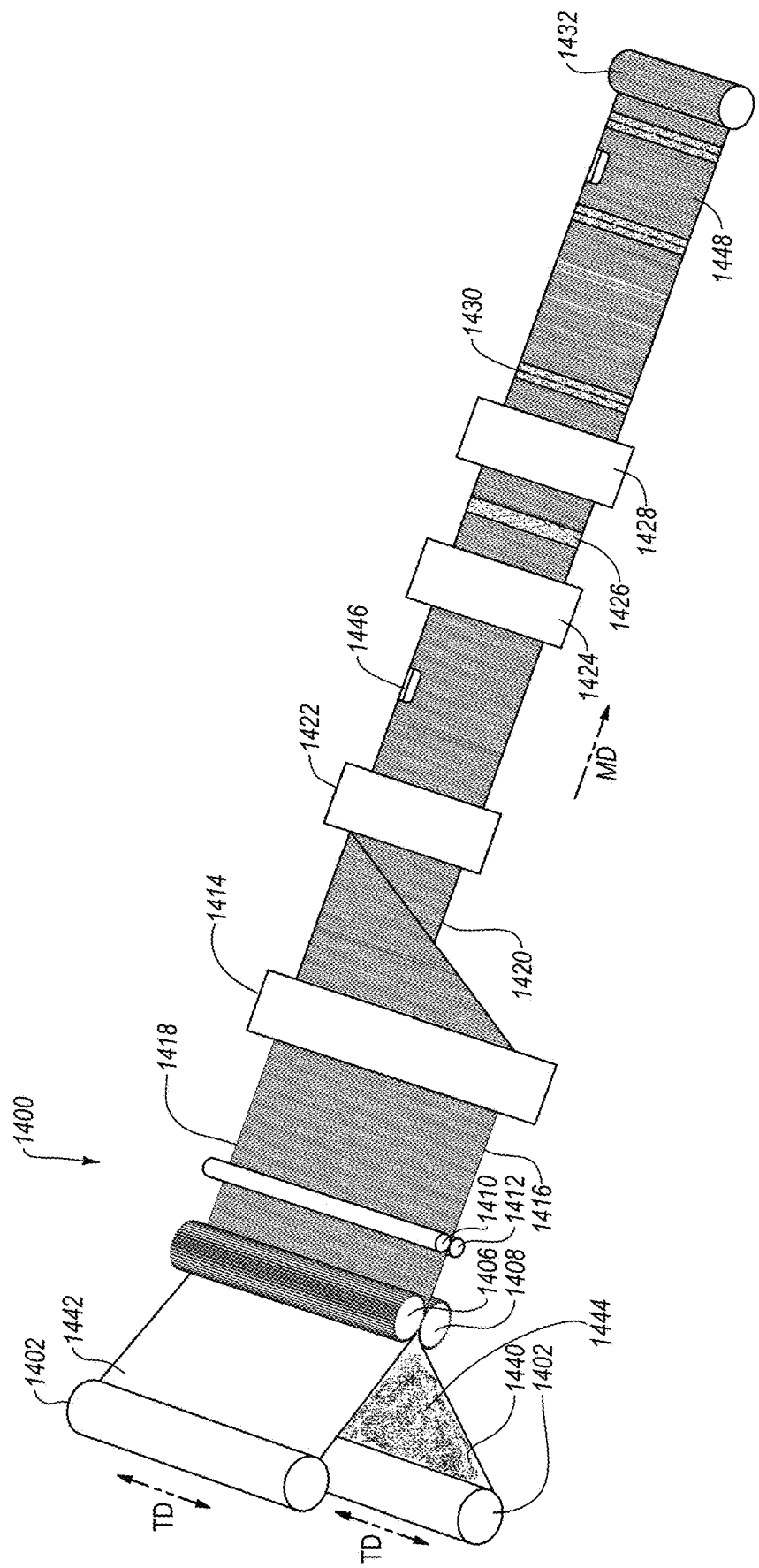
FIG. 14 illustrates a schematic diagram of another manufacturing process for producing thermoplastic bags having offset antagonistic additive components in accordance with one or more implementations.

One or more implementations of the present invention can also include methods of forming thermoplastic bags. FIGS. 13-14 and the accompanying description describe such methods. Of course, as a preliminary matter, one of ordinary skill in the art will recognize that the methods explained in detail herein can be modified. For example, various acts of the method described can be omitted or expanded, additional acts can be included, and the order of the various acts of the method described can be altered as desired.

Referring to FIG. 13, a schematic of an implementation for high-speed automated manufacturing of bags process 1300 is shown. In the illustrated implementation, the process 1300 may begin by unwinding a web 1302 of thermoplastic sheet material from a roll 1304 and advancing the web along a machine direction 1306. The unwound web 1302 may have a rectangular profile including a width that is perpendicular to the machine direction 1306 as measured between a first edge 1310 and an opposite second edge 1312. In other manufacturing environments, the process may involve extruding the web 1302 using a thermoplastic production process.

After unwinding the web 1302, the process 1300 can involve dispensing an additive component 1328 using a dispenser 1326. In one or more implementations, the additive component 1328 is additionally, or alternatively, applied using a roller or a slot cast. In one or more implementations, the additive component 1328 includes a liquid application, a powder application or any other application discussed above. As mentioned above, the process 1300 can be modified so that the act of applying the additive component can occur earlier or later than what is shown in FIG. 13. For example, in one or more implementations, the additive component 1328 can be coextruded with the web 1302 using the thermoplastic production process.

Subsequently, the process 1300 can include a folding process 1330 that involves folding the web 1302 about its width and in-line with the machine direction 1306 to provide adjacent first and second folded halves 1332, 1334. The folding of the web 1302 may cause the second edge 1312 to move adjacent to the first edge 1310 such that the two edges correspond to the opened top edge of the finished bag. The mid-width portion of the web 1302 may correspond to the reinforced bottom edge portion of the finished bag which may move in parallel with the machine direction 1306. Additionally, the folded halves 1332, 1334 of the web 1302 correspond to the first and second sidewalls of the finished bag.

Additional processing steps may be applied to produce the finished bag. In particular, the process 1300 can include a draw tape insertion process 1344 that involves inserting a draw tape into the first edge 1310 and the second edge 1312 of the web 1302.

Optionally, to bond (and optionally stretch) the halves of the web, the processing equipment may include a pair of intermeshing rollers 1346 such as those described herein above. The folded halves 1332, 1334 may be advanced along the machine direction 1306 between the intermeshing rollers 1346, which may be set into rotation in opposite rotational directions to impart the resulting bonding pattern 1350. To facilitate patterning of the folded halves 1332, 1334, the intermeshing rollers 1346 may be forced or directed against each other by, for example, hydraulic actuators. The pressure at which the rollers are pressed together may be in a first range from 30 PSI (2.04 atm) to 100 PSI (6.8 atm), a second range from 60 PSI (4.08 atm) to 90 PSI (6.12 atm), and a third range from 75 PSI (5.10 atm) to 85 PSI (5.78 atm). In one or more implementations, the pressure may be about 80 PSI (5.44 atm).

In the illustrated implementation, the intermeshing rollers 1346 may be arranged so that they are co-extensive with or wider than the width of the folded halves 1332, 1334. In one or more implementations, the bonding pattern 1350 created by intermeshing rollers 1346 may extend from proximate the folded edge to the adjacent edges 1310, 1312. To avoid imparting the bonding pattern 1350 onto the portion of the folded halves 1332, 1334 that includes the draw tape, the corresponding ends of the intermeshing rollers 1346 may be smooth and without the ridges and grooves. Thus, the adjacent edges 1310, 1312 and the corresponding portion of the folded halves 1332, 1334 proximate those edges that pass between the smooth ends of the intermeshing rollers 1346 may not be imparted with the bonding pattern 1350.

The processing equipment may include pinch rollers 1348 to accommodate the width of the folded halves 1332, 1334. To produce the finished bag, the processing equipment may further process the folded halves 1332, 1334. For example, to form the parallel side edges of the finished bag, the folded halves 1332, 1334 may proceed through a sealing operation 1352 in which heat seals 1354 may be formed between the folded edge and the adjacent edges 1310, 1312. The heat seals may fuse together the adjacent folded halves 1332, 1334. The heat seals 1354 may be spaced apart along the folded halves 1332, 1334 and in conjunction with the folded outer edge may define individual bags. The heat seals 1354 may be made with a heating device, such as, a heated knife or a sealing bars as described in greater detail below. A perforating operation 1356 may perforate the heat seals 1354 with a perforating device, such as, a perforating knife so that individual bags 1358 may be separated from the web 1302. In one or more implementations, the folded halves 1332, 1334 may be folded one or more times before the folded halves 1332, 1334 may be directed through the perforating operation. The folded halves 1332, 1334 embodying the individual bags 1358 may be wound into a roll 1360 for packaging and distribution. For example, the roll 1360 may be placed in a box or a bag for sale to a customer.

In one or more implementations of the process 1300, a cutting operation 1362 may replace the perforating operation 1356. The web is directed through a cutting operation 1362 which cuts the folded halves 1332, 1334 at location into individual bags 1358. A folding operation 1364 can then fold the individual bags one or more times to created folded bags 1358a. The folded bags 1358a can then be wound onto a roll 1366 for packaging and distribution. For example, the roll 1366 may be placed in a box or bag for sale to a customer. The bags may be interleaved prior to winding into the roll 1366. In one or more implementations, the folded halves 1332, 1334 may be folded one or more times before the folded web is cut into individual bags. In one or more implementations, the individual bags 1358 may be positioned in a box or bag, and not onto the roll 1360.

FIG. 14 illustrates an exemplary implementation of a manufacturing process for making multi-layer thermoplastic film (e.g., the first and second films 1440, 1442) having the additive component(s) 1444 disposed therein and then producing multi-layer thermoplastic bags therefrom. According to the process 1400, a first film 1440 and a second film 1442 may be unwound from stock rolls 1402, respectively, and directed along a machine direction MD. Alternatively, the first and second films 1440, 1442 may be extruded directly from one or more extrusion towers rather than stock rolls 1402.

The additive components 1444 may be applied to one or more of the first and second films 1440, 1442 on the inner sides of the first and second films 1440, 1442 (e.g., the sides of the first and second films 1440, 1442 that will be bonded together) prior to bonding the first and second films 1440, 1442. The additive component 1444 may be applied through one or more of laminating, dusting, spraying, rolling, and any other method known in the art for applying substances to films. In one or more implementations, the additive component 1444 is coextruded with the first and second films 1440, 1442.

After the additive component 1444 has been applied to one or more of the first and second films 1440, 1442, the first and second films 1440, 1442 may be passed between a pair of cylindrical intermeshing rollers 1406, 1408 to incrementally stretch and lightly laminate the initially separate first and second films 1440, 1442 to create un-bonded regions and bonded regions in at least one section of a multi-layer film (i.e., eventual sidewall of the multi-layer bag). The intermeshing rollers 1406, 1408 shown in FIG. 14 may have a construction similar to that of any of the intermeshing rollers described in U.S. Pat. No. 8,603,609. The rollers 1406, 1408 may be oriented such that longitudinal axes of the rollers are perpendicular to the machine direction. Additionally, the rollers 1406, 1408 may rotate about their longitudinal axes in opposite rotational directions. In some implementations, motors may be provided to power rotation of the rollers 1406, 1408 in a controlled manner. As the first and second films 1440, 1442 pass between the pair of rollers 1406, 1408, the ridges and/or teeth of the rollers 1406, 1408 can form the multi-layer film (i.e., eventual sidewall of the multi-layer bag).

During the manufacturing process 1400, the multi-layer film can also pass through a pair of pinch rollers 1410, 1412. The pinch rollers 1410, 1412 can be appropriately arranged to grasp the multi-layer film.

A folding operation 1414 can fold the multi-layer film to produce the sidewalls of the finished bag. The folding operation 1414 can fold the multi-layer film in half along the transverse direction. In particular, the folding operation 1414 can move a first edge 1416 adjacent to the second edge 1418, thereby creating a folded edge 1420. For example, the process may include the folding operation described in U.S. Pat. No. 8,568,283, the entire contents of which are hereby incorporated by reference in their entirety. Additionally, the folding operation 1414 may form a hem at an eventual top portion of a thermoplastic film.

To produce the finished bag, the processing equipment may further process the folded multi-layer film. In particular, a draw tape operation 1422 can insert a draw tape 1446 into the first edge 1416 and the second edge 1418 of the multi-layer film. Furthermore, a sealing operation 1424 can form the parallel side edges of the finished bag by forming heat seals 1426 between adjacent portions of the folded multi-layer lightly-laminated film. Moreover, the sealing operation 1424 can seal the hem to a sidewall of the eventual thermoplastic bag. The heat seal 1426 may strongly bond adjacent layers together in the location of the heat seal 1426 so as to tightly seal the edges (e.g., produce an at least substantially water tight seal) of the finished bag. The heat seals 1426 may be spaced apart along the folded multi-layer film to provide a desired width to the finished bags. The sealing operation 1424 can form the heat seals 1426 using a heating device, such as, a heated knife.

A perforating operation 1428 may form a perforation 1430 in the heat seals 1426 using a perforating device, such as, a perforating knife. The perforations 1430 in conjunction with the folded outer edge 1420 can define individual bags 1448 that may be separated from the multi-layer film. A roll 1432 can wind the multi-layer lightly-laminated film embodying the finished individual bags 1448 for packaging and distribution. For example, the roll 1432 may be placed into a box or bag for sale to a customer.

In still further implementations, the folded multi-layer lightly-laminated film may be cut into individual bags along the heat seals 1426 by a cutting operation. In another implementation, the folded multi-layer lightly-laminated film may be folded one or more times prior to the cutting operation. In yet another implementation, the side sealing operation 1424 may be combined with the cutting and/or perforation operations 1428.

In further implementations, the hem of the thermoplastic bag may be ring rolled and/or SELF'd to form a pattern in the hem. Moreover, the hem of the thermoplastic bag may be ring rolled and/or SELF'd prior to being folded into a hem shape and/or after being folded into a hem shape.

One will appreciate in view of the disclosure herein that the process 1400 described in relation to FIG. 14 can be modified to omit or expanded acts, or vary the order of the various acts as desired. In particular, the process 1400 can involve placing or applying an odor control component such that the odor control component is positioned in or around the hem as described below.

The present disclosure may be embodied in other specific forms without departing from its spirit or essential characteristics. For example, the illustrated and described implementations involve non-continuous (i.e., discontinuous or partially discontinuous lamination) to provide the weak bonds. In alternative implementations, the lamination may be continuous. For example, multi film layers could be coextruded so that the layers have a bond strength that provides for delamination prior to film failure to provide similar benefits to those described above. Thus, the described implementations are to be considered in all respects only as illustrative and not restrictive. The scope of the disclosure is, therefore, indicated by the appended claims rather than by the foregoing description. All changes that come within the meaning and range of equivalency of the claims are to be embraced within their scope.

What is claimed is:

1. A folded thermoplastic bag, comprising:
   a thermoplastic film folded a plurality of times to form a film stack with a plurality of layers that are separated by air gaps;
   a first additive component localized at a first position on the thermoplastic film; and
   a second additive component localized at a second position on the thermoplastic film, wherein:
      the second additive component is reactive with the first additive component;
      the second position of the second additive component is laterally offset from the first position of the first additive component in a first direction across the thermoplastic film; and
      the first position, the second position, the plurality of layers of the film stack created via the plurality of folds, and the air gaps are configured to effectively compartmentalize the first additive component and the second additive component by causing the first additive component and the second additive component to diffuse in a second direction that is across the plurality of layers and the air gaps of the film stack and perpendicular to the first direction without substantially diffusing laterally in the first direction across the thermoplastic film.

2. The folded thermoplastic bag of claim 1, further comprising one or more additional positions on the thermoplastic film directly above or directly below the first position in the second position across the film stack, wherein the first additive component has diffused to the one or more additional positions.

3. The folded thermoplastic bag of claim 2, wherein:
   the one or more additional positions are separated from each other and the first position by one or more air gaps in the second direction across the film stack; and
   the one or more additional positions are laterally offset from the second position of the second additive component in the first direction.

4. The folded thermoplastic bag of claim 3, wherein the second additive component has not substantially diffused laterally in the first direction to the first position or the one or more additional positions.

5. The folded thermoplastic bag of claim 4, further comprising one or more further positions on the thermoplastic film to which the second additive component has diffused, wherein:
   the one or more further positions are directly above or directly below the second position in the second direction across the film stack;
   the one or more further positions are separated from each other and the second position by one or more additional air gaps in the second direction across the film stack;
   the one or more further positions are laterally offset from the first position of the first additive component in the first direction; and
   the first additive component has not substantially diffused laterally in the first direction to the second position or the one or more further positions.

6. The folded thermoplastic bag of claim 5, wherein:
   the thermoplastic film comprises a first fold and a second fold;
   the first position is proximate to the first fold;
   the second position is proximate to the second fold;
   the one or more additional positions comprise three additional positions; and
   the one or more further positions comprise three further positions.

7. The folded thermoplastic bag of claim 1, wherein first and second additive components are odor controlling components.

8. The folded thermoplastic bag of claim 7, wherein the first additive component is an odor masking component and the second additive component is an odor neutralizing component.

9. The folded thermoplastic bag of claim 8, wherein the first and second additive components comprise, respectively, an oxidant and a fragrance, an absorbent and a fragrance, an acid and a base, a selectively activatable component and a trigger, or two or more different character fragrances.

10. The folded thermoplastic bag of claim 1, wherein the first additive component and the second additive component, when combined, result in a color differing from an initial color of the first additive component and an initial color of the second additive component.

11. A folded thermoplastic bag, comprising:
    a first sidewall;
    a second sidewall opposite the first sidewall and joined with the first sidewall along a first side edge, an opposite second side edge, and a bottom edge;
    a first additive component localized at a first position on the first sidewall and the second sidewall;
    a first fold proximate the first position;
    a second additive component localized at a second position on the first sidewall and the second sidewall that is laterally offset from the first position of the first additive component in a first direction across each of the first sidewall and the second sidewall, the second additive component being reactive with the first additive component;
    a second fold proximate the second position; and
    one or more additional positions on the first sidewall and the second sidewall directly above or below the first position to which the first additive component has diffused,
    wherein the first position, the second position, the first fold, the second fold, and air gaps created by the first fold and the second fold are configured to effectively compartmentalize the first additive component and the second additive component by causing the first additive component and the second additive component to diffuse in a second direction that is across layers of the first sidewall and the second sidewall created by the first fold and the second fold and that is perpendicular to the first direction without substantially diffusing laterally in the first direction across each of the first sidewall and the second sidewall.

12. The folded thermoplastic bag of claim 11, wherein the one or more additional positions are aligned with the first position in the second direction and separated by the first position by one or more air gaps created by one or more of the first fold and the second fold.

13. The folded thermoplastic bag of claim 12, wherein the second position is laterally offset in the first direction from the first position and the one or more additional positions.

14. The folded thermoplastic bag of claim 13, wherein:
the second additive component has not substantially diffused laterally in the first direction to the first position or the one or more additional positions; and
the first additive component has not substantially diffused laterally in the first direction to the second position.

15. The folded thermoplastic bag of claim 11, wherein the first additive component is an odor masking component and the second additive component is an odor neutralizing component.

16. The folded thermoplastic bag of claim 11, wherein:
the first sidewall and the second sidewall each comprise a first layer and a second layer separated by an inner layer air gap;
the first position is on the first layer; and
the first additive component has diffused across the inner layer air gap to a position on the second layer directly across the inner layer air gap from the first position.

17. A method of manufacturing a thermoplastic bag, the method comprising:
providing a thermoplastic film;
applying a first additive component to the thermoplastic film at a first position;
applying a second additive component to the thermoplastic film at a second position;
folding the thermoplastic film a plurality of times over itself to effectively compartmentalized the first additive component and the second additive component in a manner that the first position remains laterally offset from the second position in a first direction across the thermoplastic film, wherein the first additive component diffuses in a second direction that is perpendicular to the first direction to one or more additional positions directly above or below the first position without substantially diffusing laterally in the first direction to the second position; and
forming the thermoplastic film into a bag.

18. The method of claim 17, wherein:
applying the first additive component to the thermoplastic film at the first position comprises applying an odor masking component to the thermoplastic film; and
applying the second additive component to the thermoplastic film at the second position comprises applying an odor neutralizing component to the thermoplastic film.

19. The method of claim 17, further comprising:
folding the thermoplastic bag the plurality of times while maintaining the first position and the second position laterally offset from one another in the first direction; and
winding the folded thermoplastic bag about one or more additional thermoplastic bags into a roll.

20. The folded thermoplastic bag of claim 1, wherein the first additive component and the second additive component are antagonistic such that interacting decreases an effectiveness of at least one of the first additive component or the second additive component.

* * * * *